United States Patent [19]
Conway et al.

[11] Patent Number: 5,906,575
[45] Date of Patent: May 25, 1999

[54] URETHRAL URINE RETENTION DEVICE

[75] Inventors: Anthony J. Conway; Philip J. Conway; Richard D. Fryar, Jr., all of Chatfield, Minn.

[73] Assignee: Rochester Medical Corporation, Stewartville, Minn.

[21] Appl. No.: 08/637,858

[22] Filed: Apr. 25, 1996

[51] Int. Cl.⁶ .................................................. A61M 25/00
[52] U.S. Cl. .......................................................... 600/29
[58] Field of Search ................ 600/29–31; 128/DIG. 25, 128/842–843, 834–841

[56] References Cited

U.S. PATENT DOCUMENTS

| | | |
|---|---|---|
| 734,498 | 7/1903 | Bachler . |
| 2,494,393 | 1/1950 | Lamson . |
| 2,638,093 | 5/1953 | Kulick . |
| 2,649,854 | 8/1953 | Salm . |
| 3,053,257 | 9/1962 | Birtwell . |
| 3,463,141 | 8/1969 | Mozolf . |
| 3,503,400 | 3/1970 | Osthagen et al. . |
| 3,642,004 | 2/1972 | Osthagen et al. . |
| 3,646,929 | 3/1972 | Bonnar . |
| 3,768,102 | 10/1973 | Kwan-Gett et al. . |
| 3,797,478 | 3/1974 | Walsh et al. . |
| 3,841,304 | 10/1974 | Jones . |
| 4,209,010 | 6/1980 | Ward et al. . |
| 4,428,365 | 1/1984 | Hakky . |
| 4,457,299 | 7/1984 | Cornwell . |
| 4,615,692 | 10/1986 | Giacalone et al. . |

(List continued on next page.)

FOREIGN PATENT DOCUMENTS

| | | |
|---|---|---|
| 0 182 409 | 10/1985 | European Pat. Off. . |
| 0 193 406 | 2/1986 | European Pat. Off. . |
| 0 218 203 | 10/1986 | European Pat. Off. . |
| 0 407 218 A1 | 7/1990 | European Pat. Off. . |
| 352014 | 4/1922 | Germany . |
| 41 35 502 | 2/1993 | Germany . |
| 43 03 899 C2 | 8/1994 | Germany . |
| 9301516 | 11/1994 | Sweden . |
| 2 231 801 | 5/1990 | United Kingdom . |
| WO 90/04431 | 10/1988 | WIPO . |
| WO 92/11826 | 12/1991 | WIPO . |
| WO92/19192 | 11/1992 | WIPO . |
| WO 94/26215 | 5/1994 | WIPO . |
| WO 95/08968 | 9/1994 | WIPO . |
| WO 95/17862 | 12/1994 | WIPO . |
| WO96/04119 | 2/1996 | WIPO . |

OTHER PUBLICATIONS

K. K. Nielsen et al., "The Urethral Plug: A New Treatment Modality for Genuine Urinary Stress Incontinence in Women", *The Journal of Urology*, vol. 144, Nov. 1990, No. 5, pp. 1199–1202.

K. K. Nielsen et al., "The Urethral Plug II: An Alternative Treatment in Women with Genuine Urinary Stress Incontinence", *British Journal of Urology*, (1993) 72, pp. 428–432.

*Primary Examiner*—John P. Lacyk
*Assistant Examiner*—Samuel Gilbert
*Attorney, Agent, or Firm*—Merchant, Gould, Smith, Edell, Welter & Schmidt, P.A.

[57] ABSTRACT

An apparatus for sealing at least a portion of the urinary tract to prevent the unwanted discharge of urine includes a body member with a tubular member, encircled along its length by an overcoat layer, that encases a fluid, forming a cavity. The body member, with its tubular member and overcoat layer are elastically deformable from an initial "rest" or "relaxed" state, when outside of the body, where at least a portion of the overcoat layer is of a diameter equal to or greater than that of an undilated urethra. A stylet may be placed into the tubular member to serve as a guide, for elongation of the body member and to provide rigidly to the body member upon insertion into the urinary tract. There is also disclosed a method for making the apparatus of the present invention.

35 Claims, 13 Drawing Sheets

U.S. PATENT DOCUMENTS

| | | |
|---|---|---|
| 4,846,784 | 7/1989 | Haber . |
| 4,861,337 | 8/1989 | George . |
| 4,934,999 | 6/1990 | Bader . |
| 4,968,294 | 11/1990 | Salama . |
| 5,004,454 | 4/1991 | Beyar et al. . |
| 5,082,006 | 1/1992 | Jonasson . |
| 5,088,980 | 2/1992 | Leighton . |
| 5,090,424 | 2/1992 | Simon et al. . |
| 5,098,379 | 3/1992 | Conway et al. . |
| 5,112,306 | 5/1992 | Burton et al. . |
| 5,114,398 | 5/1992 | Trick et al. ............... 600/29 |
| 5,131,906 | 7/1992 | Chen . |
| 5,137,671 | 8/1992 | Conway et al. . |
| 5,140,999 | 8/1992 | Ardito . |
| 5,176,666 | 1/1993 | Conway et al. . |
| 5,242,391 | 9/1993 | Place et al. . |
| 5,261,896 | 11/1993 | Conway et al. . |
| 5,269,770 | 12/1993 | Conway et al. . |
| 5,306,226 | 4/1994 | Salama . |
| 5,334,175 | 8/1994 | Conway et al. . |
| 5,352,182 | 10/1994 | Kalb et al. . |
| 5,360,402 | 11/1994 | Conway et al. . |
| 5,370,899 | 12/1994 | Conway et al. . |
| 5,376,085 | 12/1994 | Conway et al. . |
| 5,380,312 | 1/1995 | Goulter . |
| 5,417,226 | 5/1995 | Juma ................... 600/30 X |
| 5,479,945 | 1/1996 | Simon ............... 128/DIG. 25 X |
| 5,482,740 | 1/1996 | Conway et al. . |
| 5,501,669 | 3/1996 | Conway et al. . |
| 5,513,659 | 5/1996 | Buuck et al. . |
| 5,513,660 | 5/1996 | Simon et al. . |
| 5,562,599 | 10/1996 | Beyschlag ............... 600/29 |

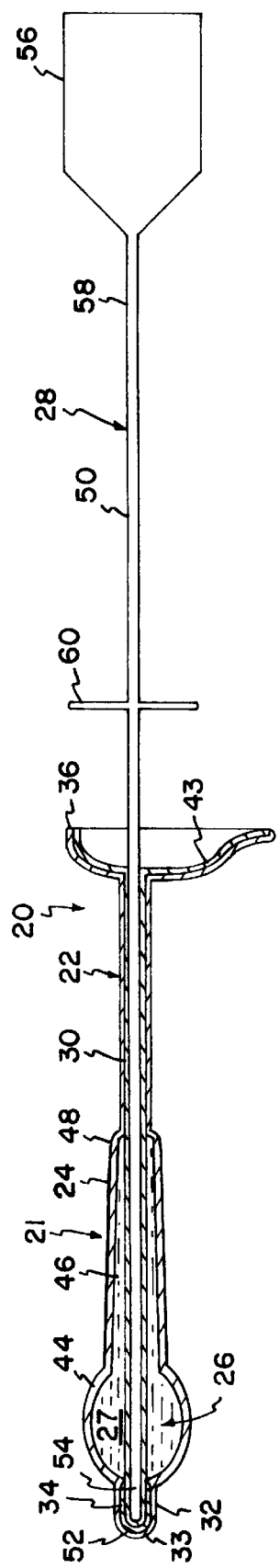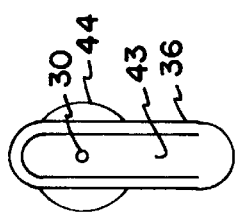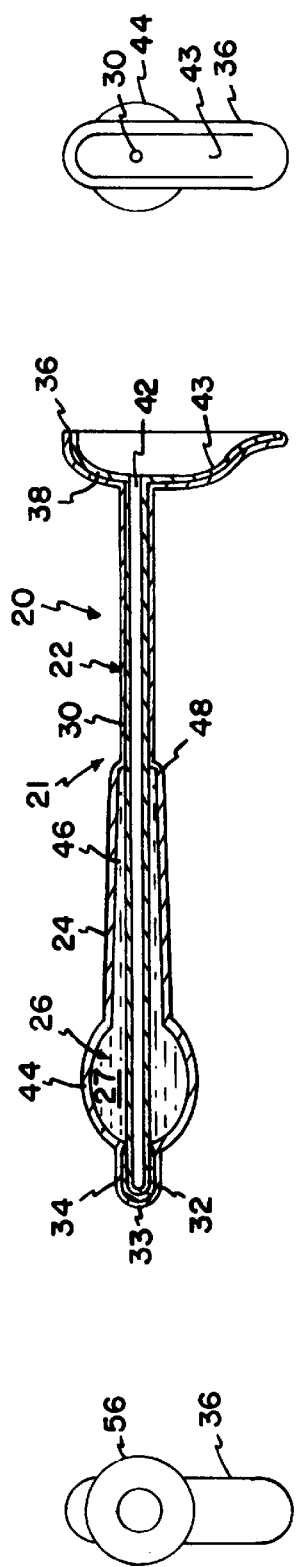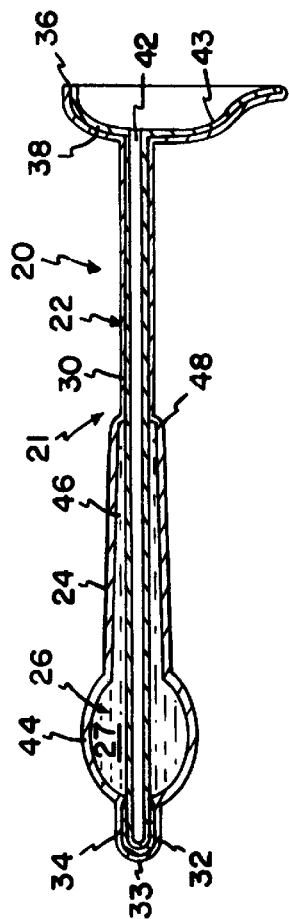

URETHRAL URINE RETENTION DEVICE

FIELD OF THE INVENTION

The present invention relates to devices for treating incontinence and other similar problems in humans, and in particular to devices, and methods for their manufacture, that serve to form a seal with at least a portion of the urinary tract, to prevent the unwanted discharge of urine from the urinary tract.

BACKGROUND OF THE INVENTION

Urinary incontinence is a problem faced by both women and men. The most common form of incontinence is known as stress incontinence, and incidences of this form of incontinence are significantly higher in women than in men. Many different forms of treatment are currently in use.

Although most incontinent people are not treated with indwelling catheters, some (for example, certain comatose patients) may not have alternatives other than using indwelling urinary catheters. Urinary catheters that are not indwelling or self-retaining, but can be intermittently inserted into the urinary tract for periodic (or intermittent) drainage, have also been used for fully draining the bladder. Such catheters usually are simple smooth tubes with rounded tips for ease of insertion and therefore are not self-retaining. A drain eyelet is present near the tip of the catheter to allow urine to enter the catheter. Such simple devices may be self-administered by the patient. Many incontinence problems can be helped by the use of such intermittently administered devices. However, for many incontinent female patients, unlike males who can wear external urinary catheters, during the period between drainage using intermittently administered catheters, diaper products must be used. Such diaper products are bulky, inconvenient, and may result in embarrassing situations for the patient if not attended to properly.

Another type of intermittently administered devices include urethral plugs. These plugs, including Foley catheters that are clamped off, are designed to be placed in the urethra and/or the bladder neck, and once in position, in the urethra or bladder neck, are expanded by inflation with gas (air), liquid, or the like. This inflation is typically performed by connecting a syringe, filled with air or liquid, with a valved tube built within the plug body. Before removal, the expanded portion of the plug, must be deflated. Both the inflation and deflation processes require the user to be capable of properly expanding and deflating the device, in order to properly insert it and remove it, and so as not to damage the urethra. These devices require manual deflation prior to removal from the urinary tract, such that an incapacitated (e.g., unconscious) user would risk overfilling of the bladder, causing severe kidney damage and even death.

These conventional plugs are relatively costly to manufacture, and disposable plugs, used once between voidance, are preferred in order to maintain sterility to avoid infection. Accordingly, manufacturing costs are a significant factor in commercial viability of disposable plug devices.

Traditionally, catheter manufacturing methods, such as those for making Foley catheters include processes that involve slipping a band of cured rubber over a double lumen latex rubber tubing and affixing the band on the double lumen tubing by dipping the band and the tubing in a suspension of latex to form an outer layer. The cost of manufacturing traditional Foley catheters has been influenced by the need to use a significant amount of hand labor to make the devices.

It will be appreciated that using such traditional methods to make catheters and other polymeric structures that have a variety of outer shapes and sizes with cavities (especially fluid-filled cavities) between the tubing and the outer layer adds significantly to the cost of production. Moreover, in many cases where a polymeric structure such as a catheter is to have a cavity filled with fluid, traditional manufacturing methods can not be used.

In addition to catheters, numerous devices such as gastronomy devices for transporting fluids into and out of various segments of the gastrointestinal system, for example, the stomach, also have a structure of an overcoat layer on an inner tubular structure defining a cavity therebetween. Many devices also require a self retention capability such as in the case of external feeding tubes.

Providing an automated method of manufacturing these polymeric structures and others would reduce the cost of many products incorporating such polymeric structures so that they would be more competitive in the market place and could be used for disposable products where low cost is essential.

The present invention includes polymeric structures, especially polymeric structures with encapsulated fluid filled cavities. In addition, the present invention provides methods for manufacturing the device of the present invention, that offer substantial advantages over traditional manufacturing methods.

SUMMARY OF THE INVENTION

The present invention improves on the prior art by providing a single use (used once between voidance) disposable urethral device, that requires minimal user skill for insertion and removal and is manufactured at a low cost. The device of the invention is preferably designed to work within the mammalian urinary tract, whose main structures include, but are not limited to, the meatus urinarius, urethra, bladder neck and bladder. More specifically, the device is preferably designed for use in the urinary tract of a human female, to block the flow of urine when deployed therein. The device is designed to exert a pressure in response to that of the structures of the urinary tract, such that the device can be removed from the urinary tract, and ultimately the body, by the user, manually initiating deformation of the device, or simply by voiding (urinating).

Voidance will normally dislodge the device of the invention in and from the urinary tract and out of the body. Accordingly, the device of the invention provides the user with an added degree of safety. For example, if the user were incapacitated, unconscious, or in other similar impaired conditions, voidance would occur naturally, such that the device would be forced out of the body. As a result of the invention, unlike the conventional plugs, urine would not remain in the bladder and back up in the kidneys, so as to severely damage the kidneys bladder and other structures of the urinary tract, or result in death to the user, until medical or other personnel could attend to removing these conventional plugs.

In human females, the urethra is about 4 cm in length, *Gray's Anatomy,* Thirty-Eighth Edition, Pearson Professional Limited (1995), and its undilated diameter is about 6 mm (0.25 in), Tortora, *Principles of Human Anatomy,* Sixth Edition, Biological Sciences Textbooks, Inc. (1992). It is commonly flaccid when in its normal undilated state. While in this undilated state, the urethra commonly has a ribbon-like shape. Upon typical dilations, such as the passage of urine during voidance, the urethra takes a rounded ovular or flattened tube shape, and expands such that the cross-sectional diameter (hereafter diameter) increases from that of the urethra in the undilated state. It is this undilated diameter of the urethra that will be referenced throughout this application as the "diameter", for purposes of uniformity, as it is well known that the urethra can be dilated into many shapes (cross sectional) of varying diameter.

The device is such that it is typically of a shape with a portion thereof having a diameter greater than that of an undilated urethra, but can be deformed by urethral wall pressure such that the diameter changes at various points along the urinary tract, for insertion, deployment and removal therefrom. Use of this device allows the user complete freedom of movement without fear of urine leaking from the urinary tract as a result of body reflexes such as sneezing, coughing, laughing, straining, freeing the user from diapers tubes or the like, that are often embarrassing to the user.

The present invention also relates to methods of making polymeric structures (i.e., urethral devices) where a cavity is formed between an inner polymeric layer and an outer polymeric layer. These polymeric structures are formed as shaped structures, and in particular, the shaping is of the cavity. These shaped cavities may be fully or partially filled with fluid (liquid or gas) or not filled at all. They may also be filled with a solid piece, or combinations of solids, liquids and/or gases.

The shaping may be achieved by coating an inner piece (e.g., a polymeric tube or shaft) with single or multiple coatings of bond-preventing agent(s), in various steps. The coating of bond-preventing agent remaining on the inner piece, before the coating of a liquid polymeric overcoat layer, is herein referred to as the "residual coating." The shape of the overcoat layer results from the varying thickness of the residual coating of the bond-preventing agent.

The residual coating, that gives shape to the overcoat layer, is achieved by coating portions of an outer surface of the inner piece with a bond-preventing agent in a plurality of dipping steps by immersing the inner piece into the bond-preventing agent to a desired depth for a desired length of time and subsequently removing the inner piece from the bond-preventing agent. The desired depth and the desired length of time for each of the plurality of dipping steps is selected so that a residual coating of bond-preventing agent of a desired thickness and shape remains on portions of the inner piece following the plurality of dipping steps.

The residual coating has a specific shape as a result of the variation between the depth of any two of the multiple of dipping steps, the number of dipping steps, the length of time between any two of the multiple dipping steps, and the varying speeds of withdrawal from the tanks of bond-preventing agent and stripping agents. By appropriate coating (with bond-preventing agent) and stripping (with stripping agents), the bond-preventing agent can be sculpted to result in desired shapes, as is achievable using conventional technology such as lathes.

The sculpted residual coating can have varying thickness, curves, and angles, and therefore, a specific desired shape. By subsequently coating the residual coating of bond-preventing agent, that coats the inner piece with a polymeric bonding composition, a shaped overcoat layer is formed wherein the shape of the overcoat layer results from the varying shape of the residual coating.

As used herein, two structures of similar shapes, but having unequal ratios of dimensions in the two structures are considered to have different shapes. For example, annular cylinders with the same inside diameter and length but different outside diameters are not considered to have the same shape.

In making the polymeric structures of the present invention, with the method of the present invention, the outside dimensions (e.g., diameter) can be made with more consistency than in similar products made by traditional manufacturing methods. The methods of the present invention make possible the highly automated process of fabricating polymeric structures with shaped gel-filled, liquid-filled or air-filled cavities, especially those with a soft, outer, elastomeric layer that can conform to the contour of a surface in contact therewith.

BRIEF DESCRIPTION OF THE DRAWINGS

The present invention will be described with reference to the accompanying drawings, wherein like reference numerals identify corresponding or like components.

In the drawings:

FIG. 1 is a cross sectional view of the present invention;

FIG. 2 is a front view of the present invention;

FIG. 3 is a rear view of the present invention;

FIG. 4 is a cross sectional view of the present invention with a stylet removed therefrom;

DETAILED DESCRIPTION OF THE DRAWINGS

Figure 5:
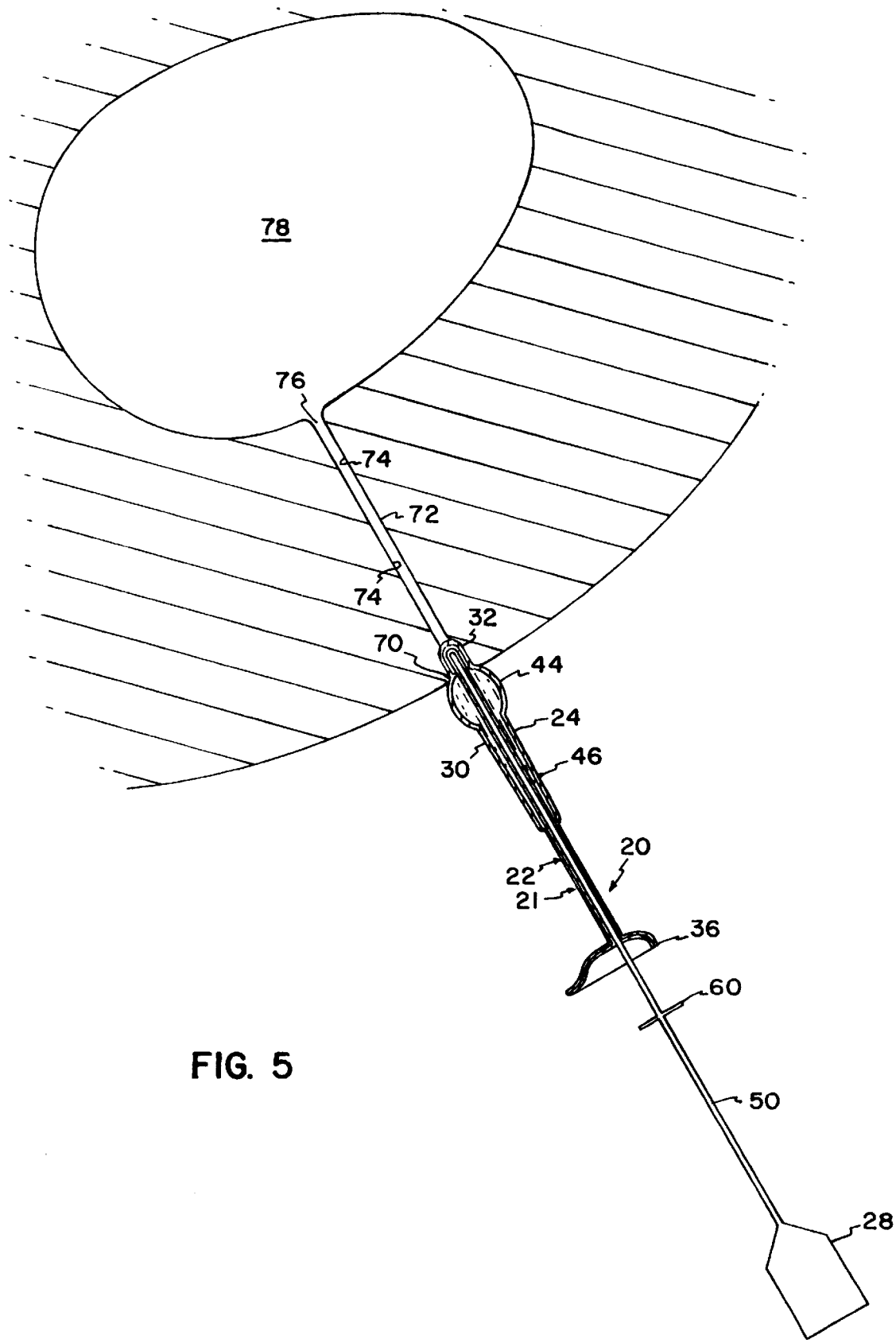
FIGS. 5–8 are cross sectional views of the present invention in use upon insertion into the urinary tract of a human female.

Turning now to FIGS. 1–4, there is shown the apparatus 20 of the invention. The apparatus 20 comprises a deformable body member 21. The body member 21 is formed of a tubular member 22, encircled along its length by an overcoat layer 24. The space between the tubular member 22 and the overcoat layer 24 defines a cavity 26, in which fluid 27 is encased. The apparatus 20 preferably also includes a removable stylet 28, received within the inner body of the tubular member 22, for deploying the apparatus 20 in the urinary tract.

The tubular member 22 includes an elongated hollow bodied shaft 30, with a tip region 32, terminating in a closed tip 33 that closes the tubular member 22 at its distal end 34. The shaft 30 terminates in a stopper member 36 at the proximal end 38 of tubular member 22. The proximal end 38 is open to allow for ingress and egress of the removable stylet 28, accommodated by the hollow inner body of the shaft 30. The stylet 28 provides the apparatus 20 with stiffness for proper insertion into the urinary tract through the urethra 72 (FIGS. 5–11), with a portion of the apparatus 20 (i.e., the tip 33 and the distal portion of the overcoat layer 24) ultimately extending into the bladder neck 76 or bladder 78 (FIGS. 5–11).

The shaft 30 is preferably tubular in shape. The inner diameter of the shaft 30, is preferably formed of a circular bore that provides the shaft 30 with a hollow inner body. This hollow inner body is substantially uniform along its entire length, and decreases at the tip region 32 (as it closes in the tip 33). The outer diameter of the shaft 30 is substantially uniform, except in the tip region 32, that is preferably greater than the remainder of the shaft 30 as this tip region 32 is thickened with additional material layers (placed onto the shaft 30 in accordance with the manufacturing process disclosed below), preferably of silicone rubber. This outer diameter of the shaft 30, even at its largest in the tip region 32, is preferably less than the diameter of the undilated urethra. This added material at the tip region 32 provides the tip region 32 with additional rigidity for ease of insertion into the urethra 72 (FIGS. 5–8), and prevents the possibility of the stylet 28 from breaking through the tip 33.

The stopper member 36, attached to the shaft 30 at the proximal end 34 of the tubular member 22, forms a common opening 42 with the shaft 30. The stopper member 36 extends outward from the shaft 30. This stopper member 36 is preferably boat-like in shape, with its length and width being greater than the diameter of the shaft 30. This boat-like shape, coupled with these dimensions allows the stopper member 36 to be gripped and retained easily by the user 80 (FIGS. 10 and 11) as well as providing a barrier against over-insertion into the urethra. Additionally, the boat-like shape allows the stopper member 36 to receive a correspondingly configured (preferably round) bar 60 on the stylet 28, that preferably abuts the inner surface 43 of the stopper member 36 (to serve to limit travel of the stylet 28 in the tubular member 22), when the body member 21, with its tubular member 22 and overcoat layer 24, is elongated and deformed during insertion of the apparatus 20 into the urinary tract.

The shaft 30, including the tip region 32 (and closed tip 33), and stopper member 36, that form the tubular member 22, are preferably an integral member, and formed a single piece during the manufacturing process (detailed below). However, multiple piece construction with fastening by conventional materials fastening techniques is also permissible.

It is preferred that the tubular member 22 is preferably made of an elastomeric material, that is also preferably medically acceptable, such as silicone rubber (elastomer), in order that it be elastically deformable. Some suitable silicone rubbers commercially available include General Electric 6030 (GE 6030) and Dow Corning Q7-4850. Silicone is also preferred, as many people, perhaps 10 to 20 percent of the world population, are allergic to latex or latex based materials, some of these allergic reactions being severe as to result in anaphylactic shock, that is fatal in extreme cases.

Additionally, silicone rubber can accommodate common surgical lubricants typically, used with the placement of urinary devices, without deteriorating or chemically breaking down. A silicone rubber tubular member 22 can be made by forming the tubular member 22 with uncured silicone rubber and then curing it, in accordance with the method detailed below. The uncured silicone rubber for making the tubular member 22 is preferably one that will result in a silicone rubber of 30–70 durometer, preferably 30–40 durometer, and can be an uncured silicone rubber dispersion of uncured silicone rubber in heptane, toluene, naphthalene, hexamethyl disiloxane or other suitable solvent. General Electric 6030 silicone rubber and Dow Corning Q7-4850 are suitable silicone rubbers for forming the dispersion.

It is to be appreciated that other suitable, medically acceptable polymeric materials may be used. These other suitable materials for manufacturing the tubular member 22 include block copolymers (such as styrene-butadiene-styrene), urethanes and latex rubbers. Additional modifications to the tubular member 22 are disclosed in the manufacturing process below.

The overcoat layer 24 encircles the shaft 30 of the tubular member 22 along a substantial portion of the length of the shaft 30. This overcoat layer 24 encases the fluid 27 in the cavity 26, such that it remains in the cavity 26 for the life of the apparatus 20. The overcoat layer 24 comprises of a bulbous portion 44, distally positioned on the shaft 30 and a sleeve portion 46, proximally positioned on the shaft 30. The overcoat layer 24 is such that its cross-sectional diameter (hereafter diameter) along at least a portion of either of its bulbous 44 and/or sleeve 46 portions, is at least equal to, and preferably greater than the diameter of the undilated urethra. The bulbous portion 44 is continuous with the sleeve portion 46. The sleeve portion 46 is preferably generally cylindrical and tapers outwardly (from rounded corners 48) to join the bulbous portion 44. The diameter of the bulbous portion 44 at its widest point is preferably greater than the diameter of the sleeve portion 46. However, the diameters of the bulbous portion 44 and the sleeve portions 46 could also be equal. The cavity 26, formed in the space between the overcoat layer 24 and the shaft 30, is preferably continuous, valveless and filled with a fluid 27, that remains encased therein.

The fluid 27 is preferably mineral oil but could also be a soft moldable semisolid such as petrolatum, petroleum jelly or a combination thereof. The fluid 27 could also be a gas, such as air or the like. The overcoat layer 24 is preferably an elastomeric material, such as silicone rubber, in order that it be elastically deformable such that the encased fluid 27 can flow from end to end therein when subject to pressure of the urethral walls that deform the overcoat layer 24 upon deployment in and removal from the urinary tract, while keeping the encased fluid from leaking from the cavity 26. The fluid 27 also serves to absorb shock from twisting or other movement of the shaft 30 when the apparatus 20 is deployed in the urinary tract. The fluid 27 also allows the overcoat layer 24 to conform to the general shape (including the diameter) of the urethra (and preferably the bladder neck upon deployment), when the urethra is either undilated (flaccid) or dilated, and any irregularities in the urethra or other portions of the urinary tract.

The overcoat layer 24 is of an elastomeric material (discussed below) that has a natural shape retaining memory. Coupled with the underlying fluid filled cavity 27, the overcoat layer 24 gently resists pressure of the urinary tract, in particular that from the urethral walls 74 (FIGS. 5–11) and the bladder neck 76 (FIGS. 5–11), by exerting a back pressure on the urethral walls 74 and the bladder neck 76. This gentle pressure engagement generally allows for the natural closure of the urethra 72 by forcing fluid 27 in the cavity 26 to the cavity portion within the bulbous portion 44 of the body member 21. At weaker points along the urinary tract, where full closure is not normally achieved (in incontinent mammals, such as humans), the body member 21 assists in attaining such closure, by providing a soft comfortable surface around which the structures of the urinary tract, for example, the urethra and bladder neck can close. At minimum, the pressure between the urethral walls 74 and the overcoat layer 24 is sufficient to seal the urethra 72, blocking the flow of urine therein. However, this resistance pressure from the overcoat layer 24 is less than that of the force of the urine being expelled from the bladder 78 during voidance, such that the force of voidance is sufficient to deform and dislodge the body member 21 from the urinary tract, and ultimately to a point outside of the body.

The overcoat layer 24 is preferably made of silicone rubber (elastomer), to be elastically deformable. Also, as stated above, silicone rubber is a medically acceptable material and is not known to give rise to the potential allergic effects of latex or latex-based materials. Additionally, silicone is preferred for it can accommodate common surgical lubricants, used with the placement of urinary devices, without deteriorating or chemically breaking down. However, other suitable materials such as block copolymers (e.g., styrene-butadiene-styrene), latex or other synthetic rubbers may also be used. The overcoat layer 24 is placed onto the tubular member 22 along the shaft 30 by the manufacturing method described below, or by other appropriate methods.

The stylet 28 is a stiff, slightly flexible rod, that is removably inserted into the tubular member 22 through the opening 42 at the proximal end 38 of the tubular member 22. The stylet 28 has a body 50 of a diameter slightly less than the inside diameter of the shaft 30 of the tubular member 22 for easy insertion and withdrawal. The body 50 has a round or blunt tip 52 at its distal end 54 and an end member 56, at the proximal end 58 of the stylet 28. The end member 56 is knob-like and shaped for a user's hand 80 (FIGS. 10 and 11) to comfortably press thereon to urge the stylet 28 into the shaft 30 of the tubular member 22, and bear against the tip 33 of the tubular member 22. A bar 60, is intermediate the tip 52 and end member 58, disposed preferably toward the proximal end 58 of the body 50 in an orientation that is generally perpendicular to the axis of the body 50. The stylet 28 is preferably made of polycarbonate or other similar plastic to give the apparatus 20 the necessary rigidity to facilitate the insertion of the apparatus 20 into the urinary tract.

The length of the stylet 28 is greater than the length of the tubular member 22, such that when the stylet body 50 is inserted all the way inside the shaft 30, with the distal end 56 of the stylet 28 bearing against the tip 33 of the tubular member 22, the end member 56 of the stylet 28 is outside of the stopper member 36. With the body member 21 in this "rest" or "relaxed" state, the bar 60 is approximately 1.5 cm away from the opening 42 at the interface of the shaft 30 and stopper member 36 (FIG. 1). Upon elongation (and deformation) of the body member 21 (tubular member 22 and overcoat layer 24), the bar 60 may be moved as far as into abutment with the stopper member 36, such that the stylet 28 is firmly within the hollow inner body of the tubular member 22 as the apparatus 20 is inserted into the urinary tract (shown in FIGS. 5–11 and described below).

The preferred embodiment of the apparatus 20 and body member 21 is small so as to be adapted for the human urinary tract. In one example, the body member 21 is preferably approximately 5 cm to 8 cm (1.97 in to 3.15 in) in length, and more preferably, approximately 4.42 cm (1.74 in), approximately 5.40 cm (2.13 in), or approximately 6.30 cm (2.48 in), to accommodate "short", "medium" and "long" urinary tracts, respectively. Along the body member 21, the tip region 32 is preferably approximately 0.25 cm to 0.76 cm (0.1 in to 0.3 in) in length, and more preferably approximately 0.50 cm (0.2 in), the bulbous portion is preferably approximately 0.76 cm to 2.03 cm (0.3 in to 0.8 in) in length, and more preferably approximately 1.52 cm (0.6 in) and the sleeve portion 46 is preferably approximately 1.24 cm to 3.63 cm (0.49 in to 1.43 in) in length, and more preferably approximately 1.50 cm (0.59 in), 2.49 cm (0.98 in), or 3.38 cm (1.33 in), while the distance between the sleeve portion 46 and the stopper member 36 on the tubular member 22 is preferably approximately 0.76 cm to 1.27 cm (0.30 in to 0.50 in), and more preferbaly approximately 1.02 cm (0.40 in). The outer diameter of the tubular member 22, at the shaft 30 and tip region 32 is preferably approximately 0.25 cm to 0.40 cm (0.10 in to 0.16 in), and more preferably approximately 0.33 cm (0.13 in), the outer diameter of the bulbous portion 44 at its widest point is preferably approximately 0.89 cm to 1.65 cm (0.35 in to 0.65 in), and more preferably approximately 1.02 cm (0.40 in), 1.27 cm (0.50 in) or 1.52 cm (0.60 in), and the outer diameter of the sleeve portion at its midpoint is preferably approximately 4.5 mm to 7.0 mm (0.18 in to 0.28 in), and more preferably approximately 5.3 mm (0.21 in), 6.0 mm (0.24 in) or 6.7 mm (0.26 in). The stopper member 36 tapers outward from the shaft 30 of the tubular member 22 to a diameter at its widest point of preferably approximately 2.3 cm (0.9 in).

Alternate embodiments of the apparatus 20, and in particular the body member 21, that operate nearly identical to the embodiment disclosed above, could be adapted for the male urinary tract, and in particular, for the urinary tract of a human male, the human male urethra being approximately 20.3 cm to 22.9 cm (8 in to 9 in) in length. These alternate embodiments, adapted for the male urinary tract, would be similar to the above described, embodiments, and may be sized smaller in length than the above described embodiments, for the tubular member, i.e., the shaft thereof, and the overcoat layer encircling the shaft, need only be of a length sufficient to extend into the spongy portion, approximately the first 15.2 cm (6 inches) from the meatus having a diameter of approximately 6.3 mm (0.25 in), of the human male urethra.

Other alternate embodiments of the apparatus 20 of the present invention include slight modifications to the body member 21, in the embodiments adapted for the urinary tracts of both the mammalian female and mammalian male to make it a retention catheter. These retention catheter embodiments include an eyelet (opening), extending through the tubular member 22, preferably at the tip region 32, to allow bodily fluid, such as urine, to enter the hollow inner body of the shaft 30 (that serves as a drainage tube) of the tubular member 22, where it would enter an additional drainage tube, this drainage tube adapted to be received by the terminal opening 42. Alternately, the stopper member 36 need not be present at all and the shaft 30 of the tubular member 22 could be extended as long as desired, to function as the drainage tube.

Turning now to FIGS. 5–11, there is shown the apparatus 20 of the invention upon deployment, use and removal from the urinary tract of a human female. The apparatus is preferably lubricated with water based lubricant, or other commonly used surgical lubricant.

Initially, as shown in FIG. 5, the apparatus 20, with the body member 21 in its rest state (unelongated and undeformed) is placed into contact with the meatus 70, such that the distal tip region 32 has entered the urethra 72. In this initial state, the overcoat layer 24, of the body member 21 with its bulbous 44 and sleeve 46 portions, is of a diameter equal to or greater then the diameter of the undilated urethra along at least a portion thereof. With the body member 21 in an unelongated state, the stylet 28, rests in the shaft 30 and tip region 32 of the tubular member 22, such that bar member 60 is approximately 1.5 cm from the stopper member 36.

Figure 6:
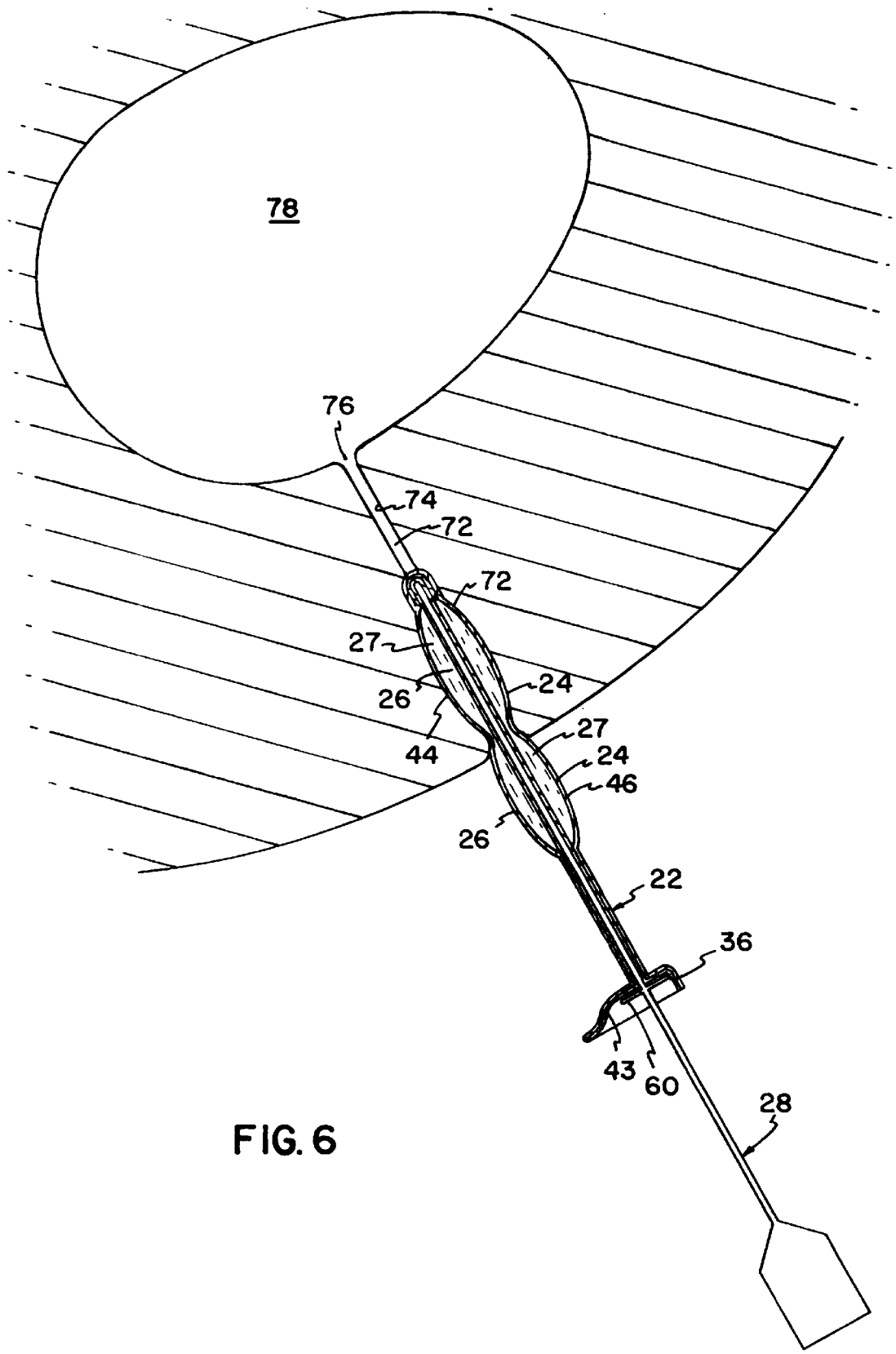

Turning to FIG. 6, there is shown the initial insertion of the apparatus 20 into the urinary tract of a human female via the urethra 72. The stylet 28 has been moved such that the bar member 60 abuts the inner surface 43 of the stopper member 36, elongating the shaft 30 of the tubular member 22. The now elongated overcoat layer 24, and the shaft 30, and tip region 32 of the tubular member 22, all narrow in diameter, and coupled with the rigidity of the stylet 28, insertion of the body member 21 in the urethra 72 may continue easily. Upon insertion, the urethral walls 74 provide their natural resistance, this resistance pressing on the overcoat layer 24, and in particular the fluid-filled bulbous portion 44, resulting in fluid 27 in the cavity 26 being pushed back into the sleeve portion 46, further reducing the bulbous portion 44 diameter for ease of insertion.

Figure 7:
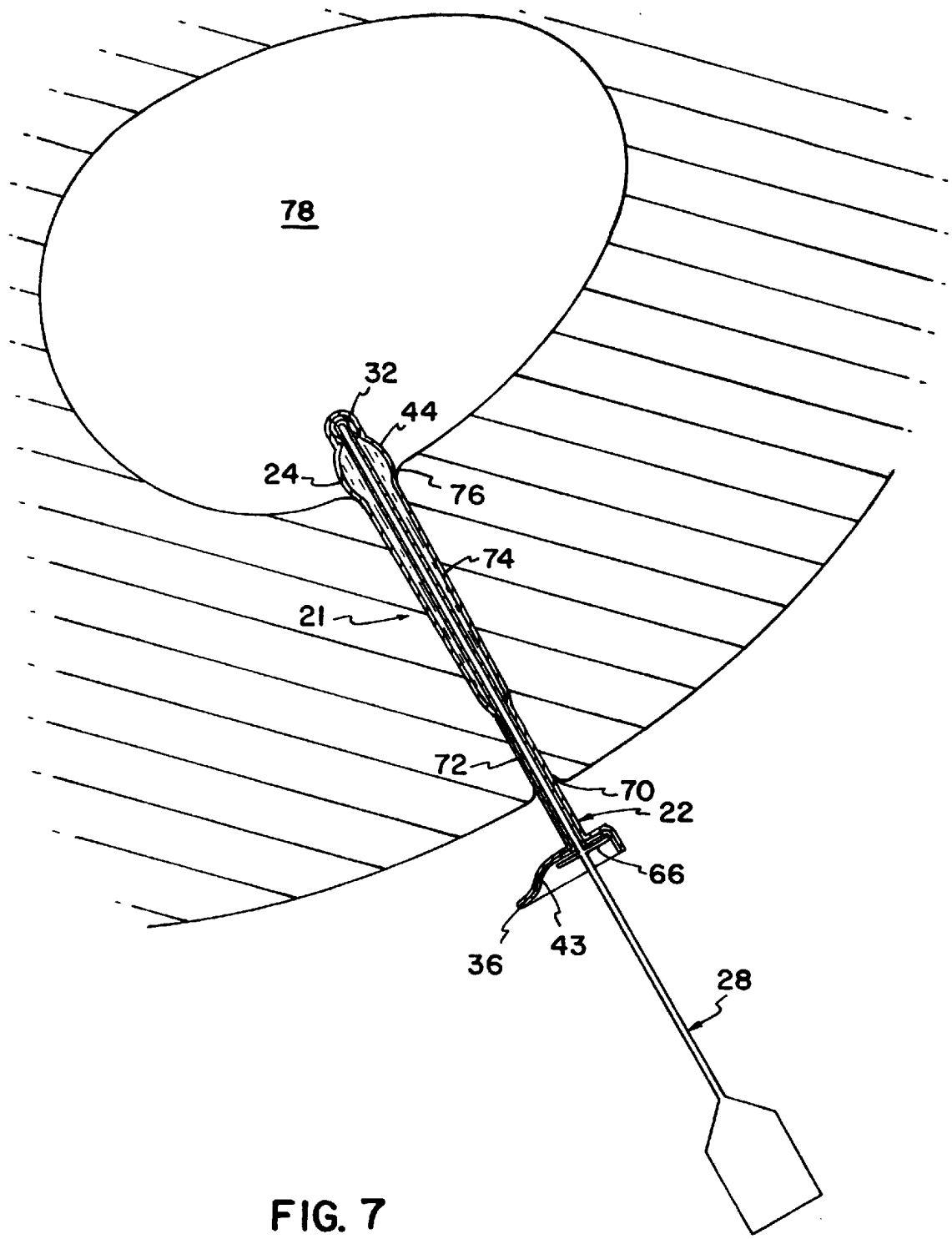
Figure 8:
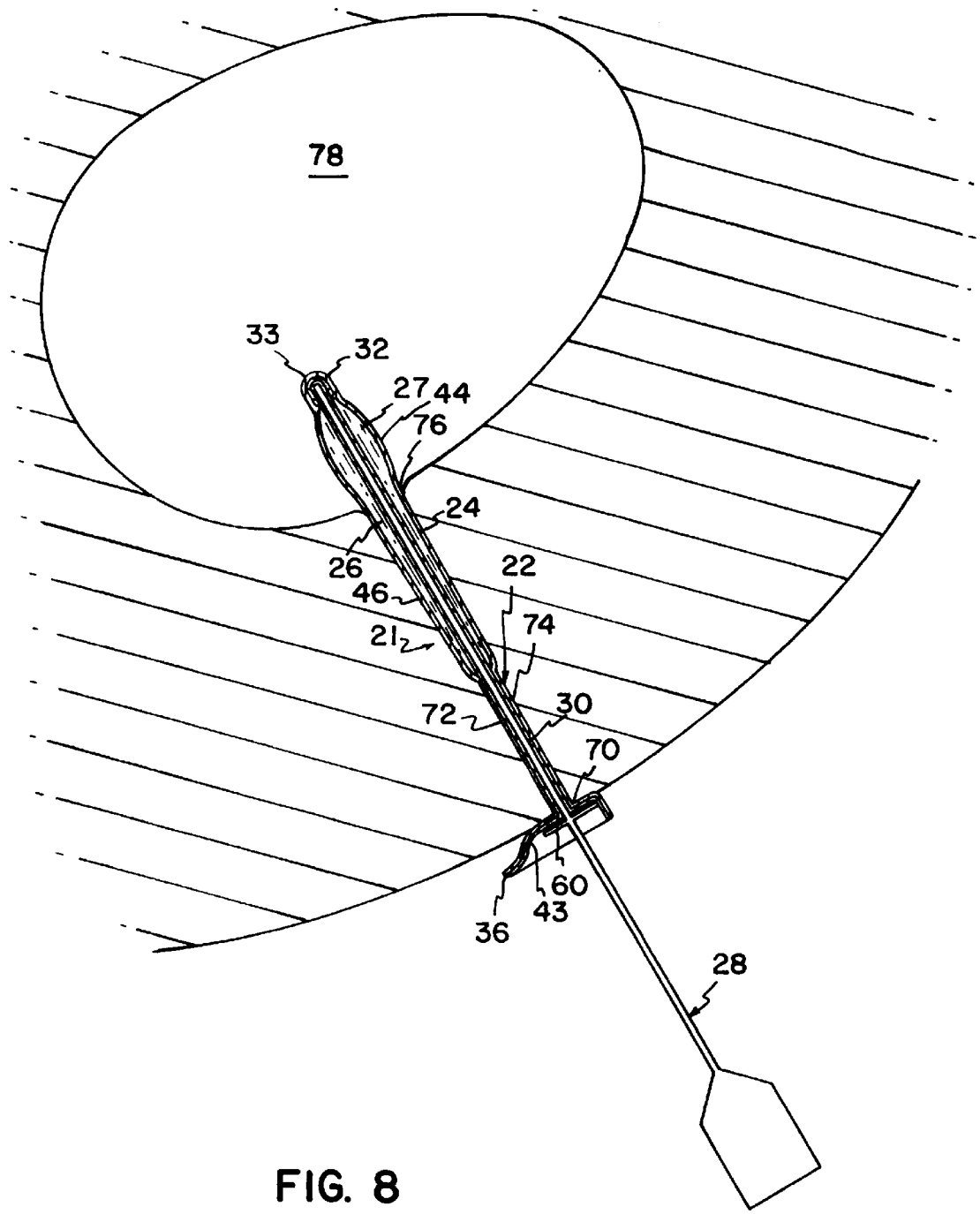

FIG. 7 details insertion proceeding until at least the tip region 32 and part of the bulbous portion 44 enters the bladder neck 76. Insertion is complete, as shown in FIG. 8, when the stopper member 36 abuts the meatus 70, the diameter of the stopper member 36 prohibits further insertion of the body member 21. Additionally, the distal tip region 32 and part of the bulbous portion 44 extends at least into the bladder neck 76, and preferably with its distal tip 33 in the bladder 78.

Figure 9:
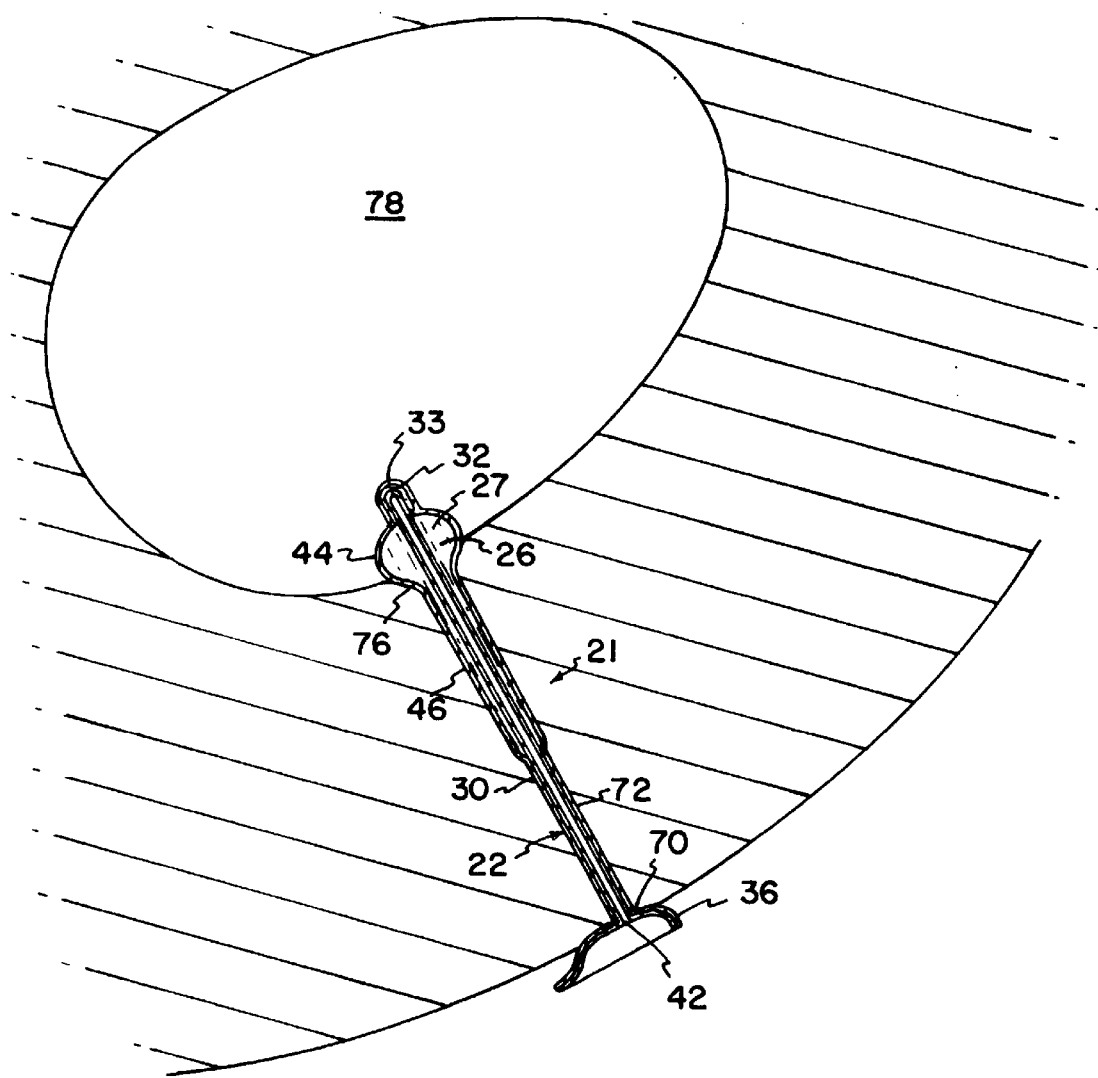
FIG. 9 is a cross sectional view of the present invention upon deployment into the urinary tract of a human female.

With insertion complete, the stylet 28 has been removed, as shown in FIG. 9. Pressure from the urethra walls 74, forces fluid 27 back into the bulbous portion 44, this urethral wall pressure may compress the overcoat layer 24 at the sleeve portion 46, such that the fluid volume in the bulbous portion 44, that has entered the bladder neck 76, or alternately, the bladder neck 76 and bladder 78, may be greater than it was prior to insertion of the apparatus 20, and the diameter of the bulbous portion 44 may be greater than it was initially, prior to insertion.

With the stylet 28 removed, the body member 21 relaxes to its unelongated state, and is now properly seated in the female urinary tract. The entire overcoat layer 24 is now in the urinary tract, with part of the bulbous portion 44, and the tip region 32 of the shaft 30 extending into the bladder neck 76 or bladder 78, while part of the bulbous portion 44 seats at the bladder neck 76, effectively blocking urine flow and effectively retaining the body member 21 in the urinary tract. The natural memory of the overcoat layer 24 coupled with underlying fluid filled cavity 26 serves to maintain a gentle pressure, exerted by the bulbous 44 and sleeve 46 portions within the urethra 72, on the urethral walls 74, in response to the pressure exerted by the urethral walls. The resistance of this overcoat layer 24 is such that it conforms to the ribbon-like shape of the urethra 72, effectively sealing the urethra 72, blocking urine flow therethrough, in addition to the bladder neck 76, thus blocking urine flow from the bladder. This sealing by the body member 21 at the urethera 72 and bladder neck 76 serves to retain urine in the urinary tract until the body member 21 is removed manually (as detailed below), or by voidance (detailed above).

Figure 10:
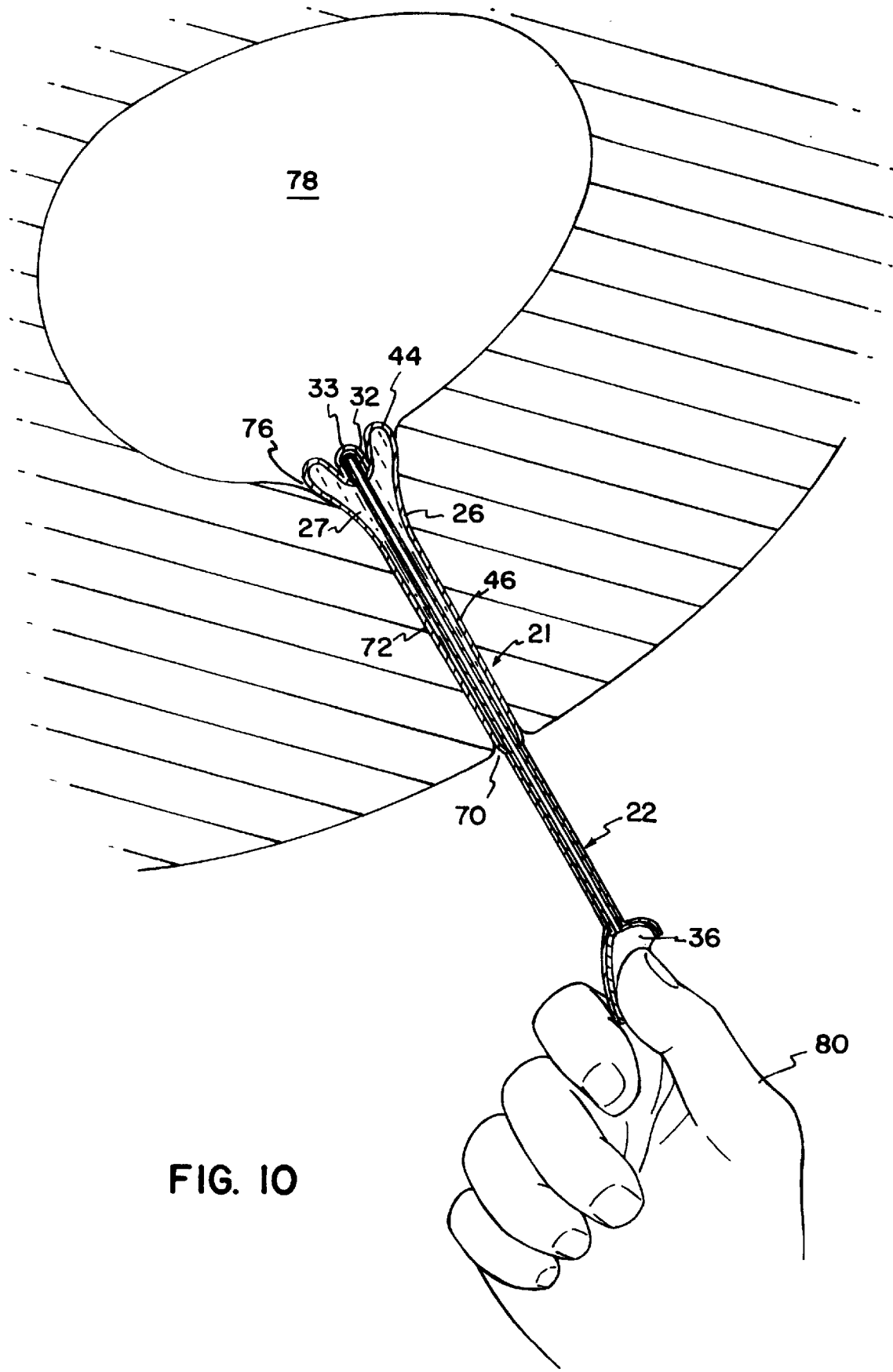
FIGS. 10 and 11 are cross sectional views of the apparatus of the present invention upon removal from the urinary tract of human female.
Figure 11:
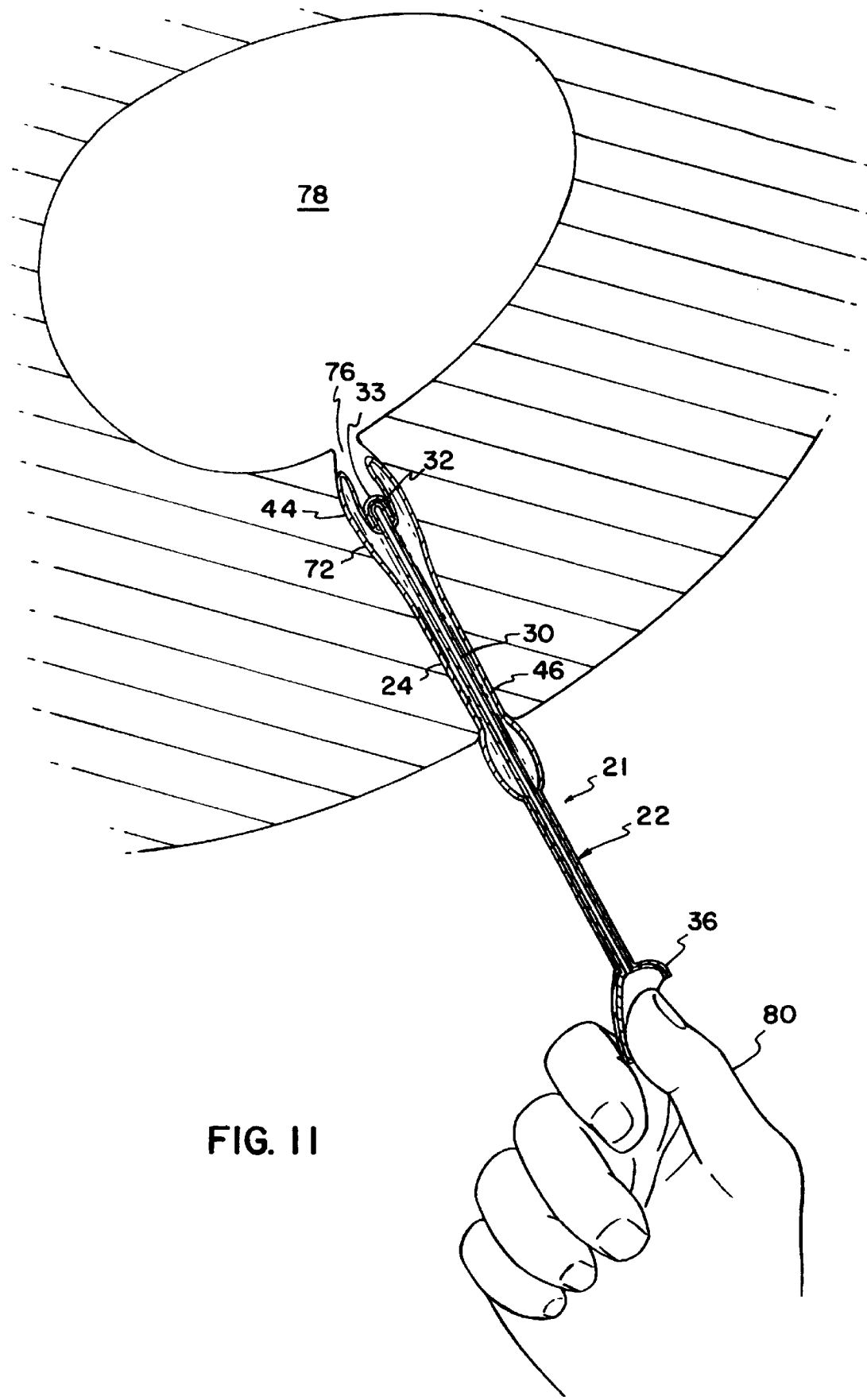

When voidance is desired, as shown in FIG. 10, the user 80 pulls on the stopper member 36 and the tubular member 22 (shaft 30 and tip region 32) is elongated. This elongation puts pressure on the overcoat layer 24 surrounding the bulbous portion 44, and forces fluid from the bulbous portion 44 into the sleeve portion 46, reducing the diameter of the bulbous portion 44. FIG. 11 shows the continued outward pulling of the stopper member 36 by the user 80, such that part of the sleeve portion 46 emerges from the meatus 70. The pressure from the urethral walls 74 and bladder neck 76 forces fluid 27 to flow into the sleeve portion 46, that expands to accommodate this excess fluid 27. The outward pulling may also cause part of the bulbous portion 44 to extend beyond the distal tip 33, as the result of the pressure from the urethral walls 74, that force fluid 27 into the sleeve portion 46. The pulling continues until the body member 21 has been completely removed from the urinary tract.

While the removal procedure detailed above and illustrated in FIGS. 10 and 11 is preferred, removal of the body member 21 from the urinary tract by voidance (as discussed above) is also permissible.

Method of Making Polymeric Shapes

To illustrate the application of the present method to forming a shaped, polymeric structure, the embodiment of making a urethral urine retention device (the apparatus 20) of the present invention is described as follows. The body member 21 of the apparatus 20 of the present invention may have components of various lengths and diameters, for example, due to the varied sizes of the human urinary tract. The manufacturing method described below is general so as to be applicable for producing various sized devices in accordance with the present invention.

Figure 12:
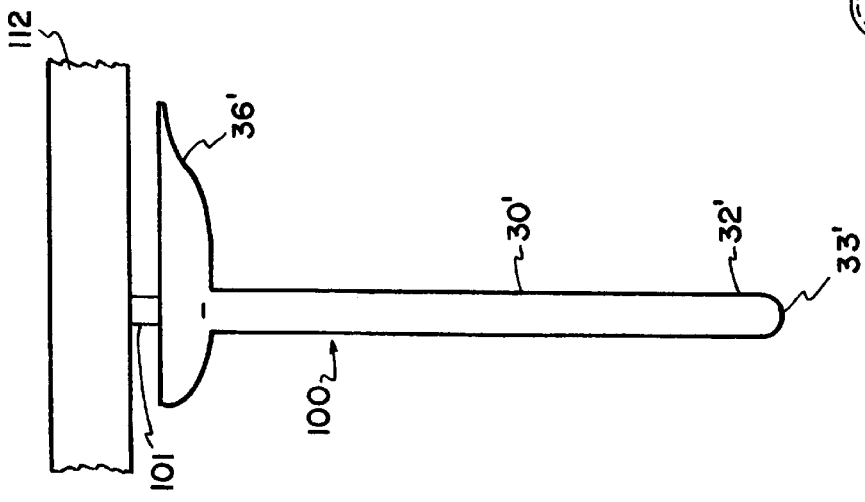
FIG. 12 is a side view of a mandrel for making an embodiment of the present invention.

Referring now to FIG. 12, there is shown a mandrel 100 on which the tubular member 22 and overcoat layer 24, forming the body member 21, is formed. The mandrel 100 (shown attached to a pallet 112 by a connector 101) is shaped to include portions corresponding to the shaft 30', tip region 32' (with closed tip 33') and stopper member 36'. Multiple mandrels, identical to the mandrel 100, shown in the drawing figures, are used simultaneously in the manufacturing process. The mandrels 100 are preferably made of a metal or alloy such as stainless steel or aluminum. The mandrels 100 are preferably coated with a polymer having low surface energy, such as tetrafluroethylene (e.g., TEFLON) so that the completed body members 21 (polymeric structures) can be readily removed from the mandrels 100.

Figure 13:
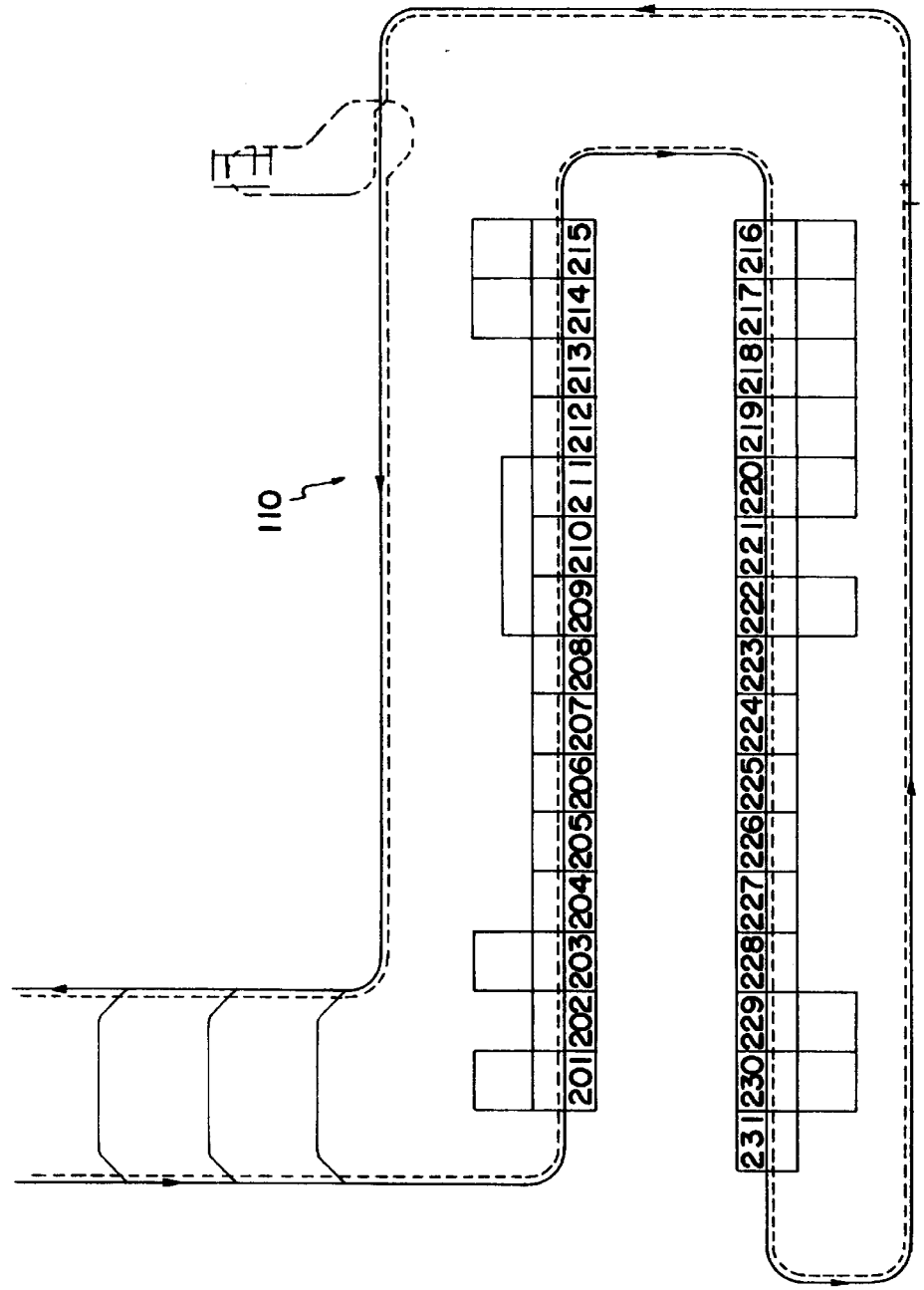
FIG. 13 is a schematic representation of a production line including processing stations for manufacturing the present invention.

Referring also to FIG. 13, there is shown a schematic representation of a preferred production line 110 which is virtually fully automated. The automated production line 110 includes one or more pallets 112 that move through various stations 201–231, at predetermined, preferably equivalent time intervals, where the various processing steps are performed. The intervals are preferably ten minutes, however, other time intervals of equal or unequal times are also permissible.

Figure 14:
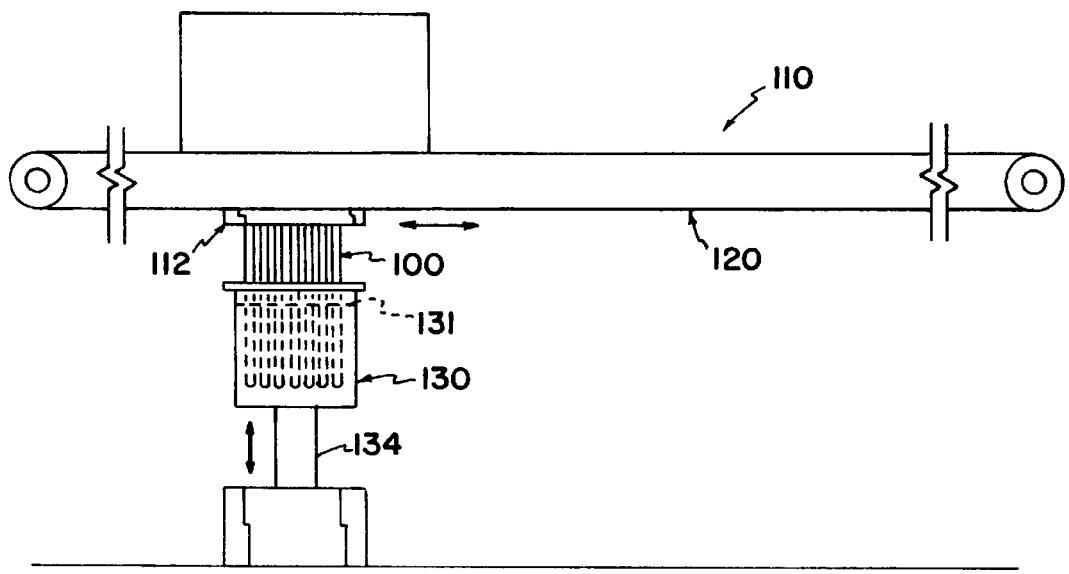
FIG. 14 is a schematic illustration of an apparatus, including a dip tank and a transport mechanism used in the production of the present invention.

Turning also to FIG. 14, there is shown the processing of multiple mandrels 100 such that multiple body members 21 (polymeric structures) can be produced simultaneously. Each pallet 112 holds a plurality of elongated mandrels 100, preferably four hundred, typically arranged in rows of twenty by twenty, with the mandrels 100 being spaced apart approximately one inch (2.54 cm). The moveable pallet 112 is attached to a transport mechanism 120 for moving the pallets 112 between the processing stations 201–231 (FIG. 13) for various processing operations. Those processing stations include dip tanks (FIG. 14), drying units, curing ovens, cooling mechanisms, etc.

In FIG. 14, there is shown a dip tank 130, that is used at processing stations 201, 203, 214–217 and 219 (FIG. 13) where dipping occurs. Each of the respective dip tanks, at processing stations employing dip tanks 201, 203, 214–217 and 219 (FIG. 13), are configured similarly to the dip tank 130 illustrated in FIG. 14, except the tanks will hold different solutions 131 (detailed below) for the requisite processing steps. The mandrels 100 are processed in the dip tank 130 by immersion in the requisite solutions when the respective dip tank is raised and lowered by a lift mechanism 134. This raising and lowering of the dip tank, for purposes of this disclosure will constitute a "dip" or a "dipping". Unless otherwise stated, the times provided for the "dip" or "dipping" will include the entire raising and lowering time for the dip tank, and unless otherwise stated, the raising time and the lowering time for the dip tank will be approximately equal.

The processing steps attained by dipping the mandrels 100 in the solutions in these dip tanks, along with drying, curing and cooling at various intervals throughout the manufacturing process creates a polymeric tubular member, shaped residual coating of a bond-preventing agent, and a polymeric overcoat layer, formed on the polymeric tubular member that is formed on the mandrel 100, at different stages of the process, resulting in a shaped structure (body member 21) of the present invention.

Figure 15:
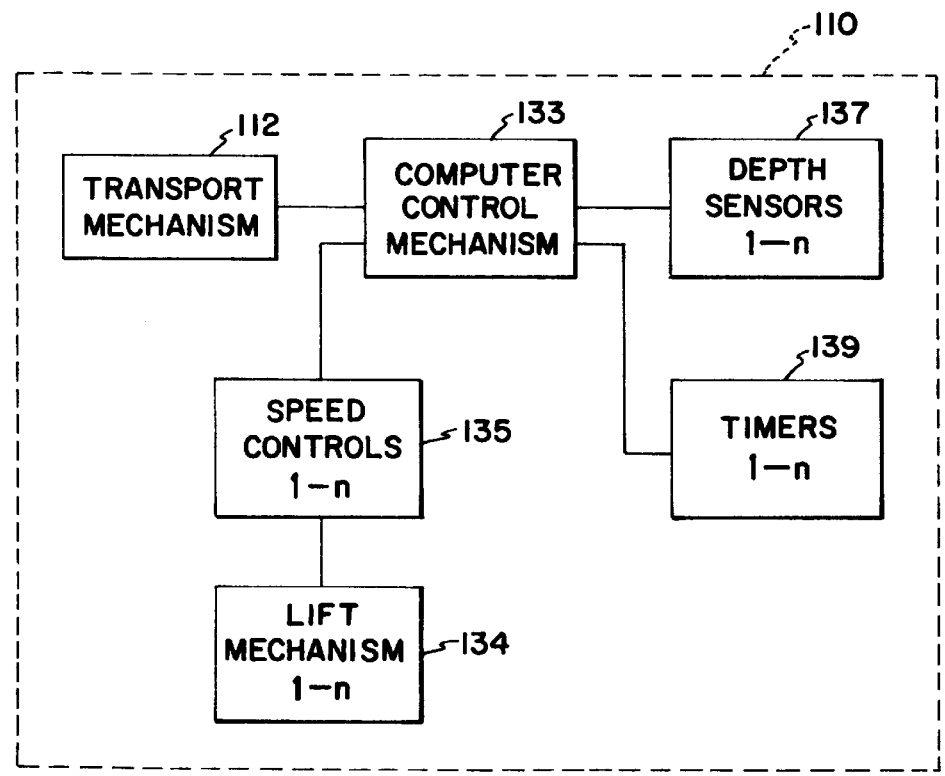
FIG. 15 is a schematic representation of the automated controls for the apparatus shown in FIG. 14, used to automate the production of the present invention.

Movement of the pallet(s) 112 is/are preferably controlled by an output from a computer control mechanism 133, illustrated schematically in FIG. 15, which are directed to the transport mechanism 120. The computer control mechanism 133 provides outputs for the multiple (1–n) lift mechanisms 134, speed controls 135, depth sensors 137 and timers 139, associated with each dip tank.

Stations with dip tanks (indicated above and below) are such that each of the respective dip tanks are raised and lowered by associated lift mechanisms 134. The lift mechanisms 134 are also preferably controlled by outputs from the computer control mechanism 133. Each of the lift mechanisms includes a speed control 135 capable of modulating the rate at which the respective dip tank is raised and lowered so that the speed at which the respective mandrels are immersed into and withdrawn from the respective fluid within the respective dip tank can be varied, either continuously or intermittently, and either during one dipping or between different dippings. The computer control mechanism 133 also receives inputs from depth sensors 137 within each of the respective dip tanks. The depth sensors 137, preferably ultrasonic depth sensors 137, are capable of providing an input to the computer control mechanism 133, which enables the computer control mechanism 133 to determine when the mandrels 100 are immersed to a desired depth in each respective dip tank.

Timers 139 are also provided for each of the respective dip tanks in order to provide inputs to the computer control mechanism 133 so that the computer control mechanism 133 can determine when a desired period of time has elapsed. A computer program is provided, that moves the pallet(s) 112 along the mechanized production line 110 and raises and lowers the respective dip tanks at predetermined times, at predetermined rates of speeds, and to predetermined locations and/or heights to enable the mechanized production line 110 to produce a plurality of completed polymeric structures (body members 21) (FIGS. 1–4) by dipping the mandrels 100 in various dip tanks having various solutions.

In alternate embodiments, the mechanized production line 110 may have a series of pallets (not shown) which are moved along an alternate transport mechanism (not shown) in series.

If desired, the polymeric tubular member 22 can also be provided by either forming it from suitable tubing (e.g., medically adaptable silicone rubber tubing) purchased from a commercially available supplier (e.g., Dow Corning), or made by an extrusion process known to those skilled in the art. The tubing is then cut to length, with the tip region 32 attached thereto by adhesives or other equivalent polymer joining methods, and the stopper member 34 secured thereon by polymer working methods known in the art. The tubular member 22 is then secured to support rods (not shown) in place of mandrels 100, which can be attached to the pallet 112. Processing of this pre-formed tubular member would begin at step (I), in station 214 (FIG. 13) detailed below.

Figure 16:
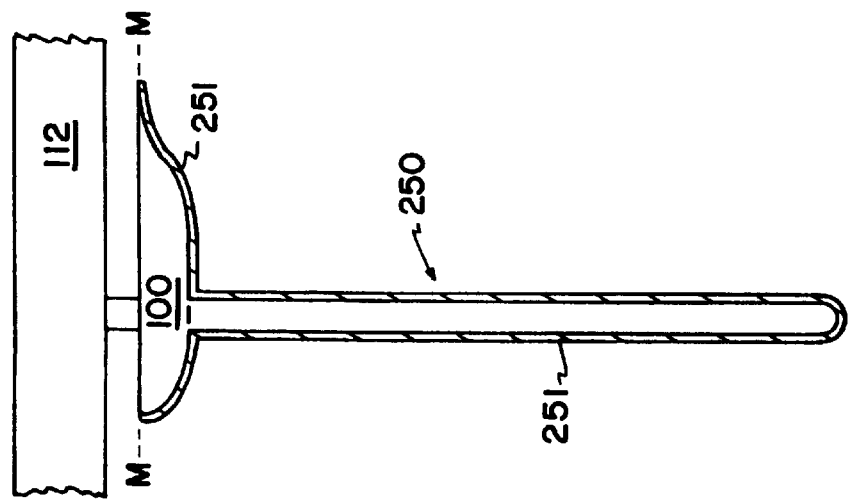

Referring to FIGS. 12 and 16–22, in a preferred embodiment of the present method wherein the manufacturing process is automated for mass production of body members 21 (polymeric structures) of the invention. Approximately four hundred TEFLON-coated stainless steel mandrels 100 (FIG. 14) are mounted vertically on a moveable pallet 112. The pallet 112 is then moved via a transport mechanism 120 through a series of processing stations 201–231 (FIG. 13). It is preferred that each pallet 112 remain within each processing station 201–231 for approximately a 10 minute interval, with approximately 30 seconds between each 10 minute interval for moving between stations. In cases where individual processing stations are a single unit (e.g., stations 209–211 are a single cure oven, and stations 226–231 are a single petrolatum or petroleum jelly filled tank), the approximately thirty seconds of movement time is built into the total time in the processing station(s). This timing and movement between processing stations is accomplished as the production process is under computer control and subject to a specific computer program or programs. The ambient temperature on the production line (also referred to as the ambient environment) is approximately 15.5° C. (60° F.). One manufacturing embodiment is as follows:

(A) The pallet 112 with a bare mandrel 100 (FIG. 12) is transported to station 201 over a first tank 130 (FIG. 14), that contains a polymeric bonding composition, e.g., an uncured silicone dispersion—a dispersion of General Electric 6030 Silicone (GE 6030) or Dow Corning Q7-4850 Silicone (Dow Corning Q7-4850) in heptane, a solvent. The dip tank 130 is then raised to immerse the mandrels 100 in the uncured silicone dispersion to a depth to cover substantially the whole length of the mandrels 100, such that the uncured silicone rubber dispersion covers the mandrels 100 up to the level of dash line M (FIG. 16). The dip tank 130 is then lowered, this raising and lowering constituting a single "dip", such a "dip" in this instance being approximately one minute. The now coated mandrels 100 are dried for approximately one minute and thirty seconds, allowing for evaporation of the solvent. The drying is by air, at approximately 21° C. (70° F.) being blown through the processing station 201. The one minute "dip", followed by the one minute and thirty second "dry" is repeated preferably three times. This "dip" and "dry" series, results in an intermediate polymeric structure 250 having a first polymeric coating 251 on the mandrel 100 of a thickness that corresponds to an inner tube thickness of about 0.76 mm (0.030 in), plus or minus 0.25 mm (0.010 in).

(B) The pallet 112 is then transported to station 202, into a drying station, where the coated mandrels 100 are dried for approximately ten minutes (the interval period), allowing for evaporation of the solvent. The drying is by air, at approximately 21° C. (70° F.) being blown through the processing station 202.

Figure 17:
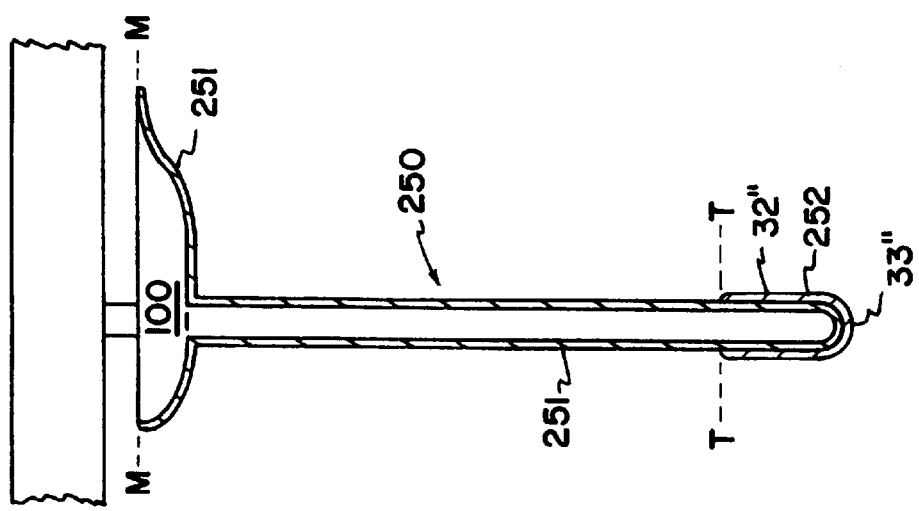

(C) The pallet 112 is moved to station 203 over a second dip tank (similar to the dip tank at station 201 and as shown in FIG. 14), that contains a polymeric bonding composition, e.g., an uncured silicone dispersion—a dispersion of General Electric 6030 Silicone (GE 6030) or Dow Corning Q7-4850 Silicone (Dow Corning Q7-4850) in heptane, a solvent. In an approximately one minute "dip", the dip tank is then raised to immerse the mandrels 100 in the uncured silicone dispersion to a level corresponding to dashed line T (FIG. 17). The dip tank is then lowered, completing the "dip", and the now coated mandrels 100 are dried for approximately one minute and thirty seconds, allowing for evaporation of the solvent. The drying is by air, at approximately 21° C. (70° F.) being blown through the processing station 203. The one minute "dip", followed by the one minute and thirty second dry is repeated preferably three times. These "dip" and drying steps, result in a second polymeric coating 252 of a thickness at the intermediate tip region 32" (including the intermediate tip 33") preferably about 0.76 mm (0.030 in) (FIG. 17).

(D) The pallet 112 is then transported to stations 204–207 where the coated mandrels are dried for approximately 40 minutes, allowing for evaporation of the solvent. The drying is by air, at approximately 21° C. (70° F.) being blown through the processing stations 204–207.

(E) The pallet 112 is then moved to an empty station 208, where the coated mandrels 100 dry in the ambient environment.

(F) The pallet 112 then moves to a cure oven, formed by the combination of stations 209–211. This cure oven is at 110° C. (230° F.), and the coated mandrels remain therein for approximately thirty minutes, such that the silicone on the mandrels 100 can properly cure.

(G) Next, the pallet 112 is moved to station 212, where it is dipped into a tank of water at 15.5° C. (60° F.), for preferably a single approximately four minute "dip". This "dip" is performed to cool the mandrels 100.

(H) The pallet 112 is then moved to an empty station 213, where the coated mandrels 100 dry in the ambient environment.

Figure 18:
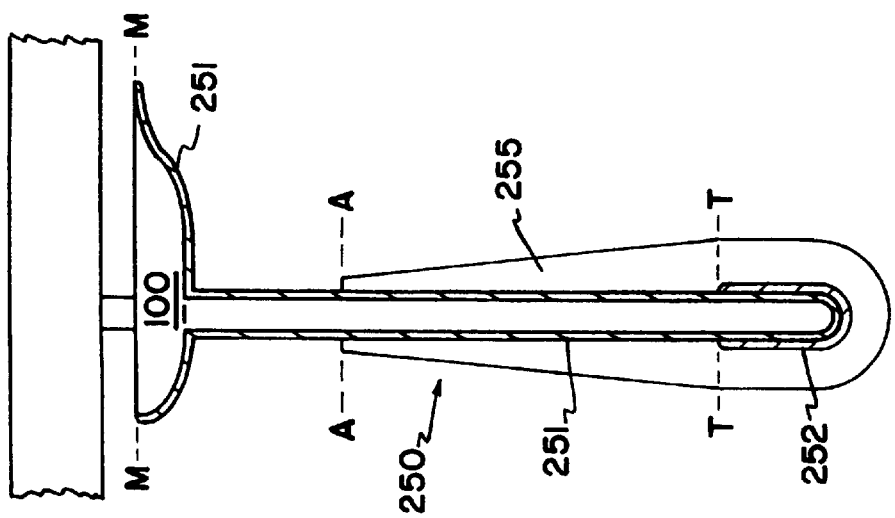
FIGS. 16–22 are cross sectional views of the manufacturing steps used in making the apparatus of the present invention.

(I) The pallet 112 is then moved over a dip tank (similar to the dip tank 130 at station 201, as shown in FIG. 14), at station 214. Stations 214–218 are isolated from the other stations on the production line 110, to accommodate air being blown therethrough at approximately 15.5° C. (60° F.). The dip tank at station 214 contains a bond-preventing agent, such as petroleum jelly or petrolatum, preferably a liquid petrolatum mixture at about 52° C. (about 125° F.). The mixture will include Perfecta™ Petrolatum USP (from Sonneborn Petrolatums, Sonneborn Div., Witco Chemical Corp., New York, N.Y.). The tank is raised so as to immerse the coated mandrels 100 to a depth up to dashed line A, as shown in FIG. 18. The dip tank is then lowered, such that coated mandrel 100 is further coated with a first coating 255 of petrolatum. This "dip" in the dip tank is approximately thirty seconds long, and once the "dip" is complete, the coated mandrels 100 are dried and cooled for anywhere between 60 and 150 seconds. The drying is by air, at approximately 15.5° C. (60° F.) being blown through the processing station 214. The "dip" and subsequent drying steps are repeated, preferably three times until the first coating 255 is built up to a desired thickness. Preferably, this thickness is about 0.76 mm to 1.78 mm (0.030 in to 0.070 in). The "dips" in this processing step are such that some rundown or sag in the liquid petrolatum or petroleum jelly occurs prior to its solidifying, as it cools on the surface of the coated mandrel 100, causing the first coating 255 to be somewhat tapered. The amount of the taper is controllable by controlling the withdraw speed of the dip tank and the ambient temperature.

Figure 19:
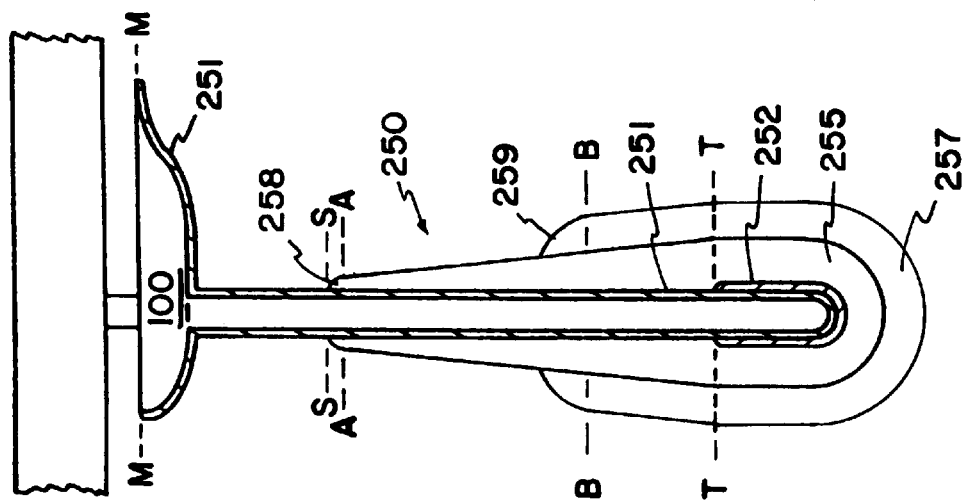
Figure 22:
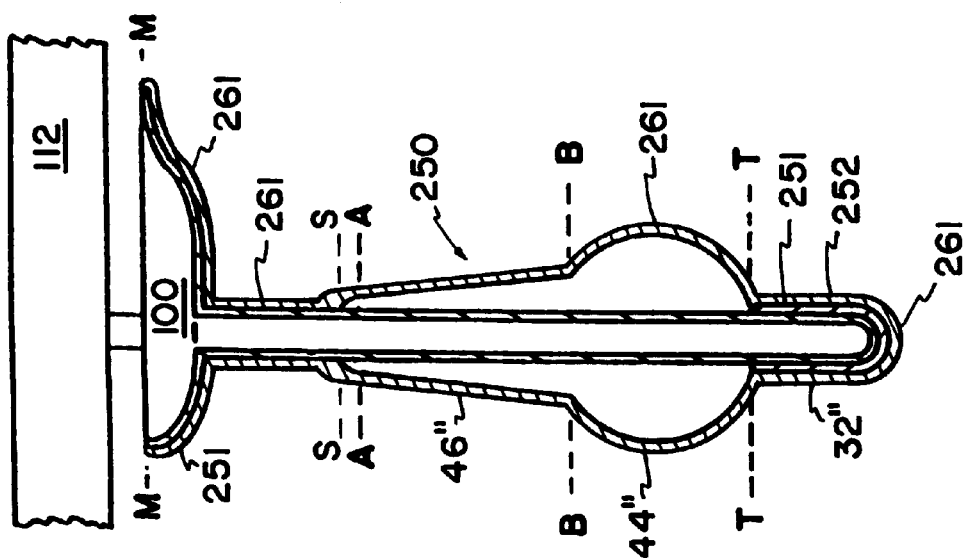

(J) The pallet 112 is then moved over a dip tank (similar to the dip tank 130 at station 201, as shown in FIG. 14), at station 215 which contains a bond-preventing agent, such as petroleum jelly or petrolatum, preferably a liquid petrolatum mixture at about 52° C. (125° F.). The mixture will include Perfecta™ Petrolatum USP (from Sonneborn Petrolatums, Sonneborn Div., Witco Chemical Corp., New York, N.Y.). The tank is raised so as to immerse the coated mandrels 100 to a depth up to dashed line B, as shown in FIG. 19. The dip tank is then lowered, such that coated mandrel 100 is further coated with a second coating 257 of petrolatum. This "dip" in the dip tank is approximately thirty seconds long, and once the "dip" is complete, the coated mandrels 100 are dried and cooled for anywhere between 60 and 150 seconds. The drying is by air, at approximately 15.5° C. (60° F.) being blown through the processing station 215. The "dip" and subsequent drying steps are repeated, preferably three times until the second coating 257 is built up to an additional thickness. Preferably, this additional thickness is about 0.76 mm to 1.78 mm (0.030 in to 0.070 in).

Figure 21:
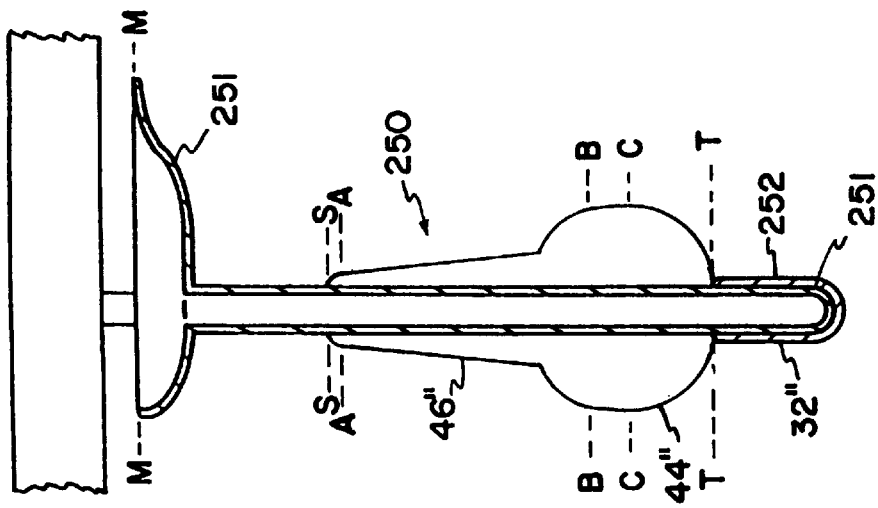
Figure 20:
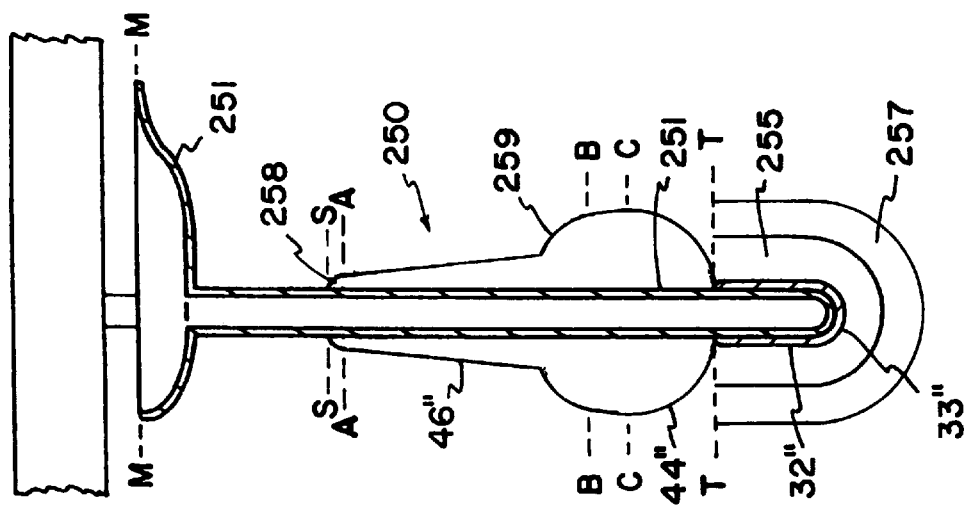

(K) The pallet 112 is then automatically advanced to station 216 and stopped over a dip tank (similar to the dip tank 130 at station 201, as shown in FIG. 14), that contains hot USP petrolatum or petroleum jelly heated to about 88° C. (190° F.). This hot USP petrolatum (or petroleum jelly) serves as both a shaping and a stripping agent. Controlled dipping in this hot USP petrolatum allows for the first 255 and second 257 petrolatum coatings to be largely removed in a desired manner (by material addition and stripping). The dip tank is raised so as to immerse the coated mandrel 100 in the super-heated petrolatum for approximately five seconds to dashed line S. The dip tank is immediately lowered (pulled-back) to dashed line C, such that portions of the petrolatum are left on top of the first coating 255, forming first shoulders 258 at the top edges of the first coating 255 (indicated by dashed line A), and portions of the petrolatum left on the second coating 257, form second shoulders 259 at the top edges of the second coating 257 (indicated by dashed line B). This pull-back to dashed line C takes a total of about five seconds, and serves to provide shape to the intermediate sleeve portion 46" and part of the intermediate bulbous potion 44", as shown in FIG. 20. This lowering (pull-back) continues, for approximately twenty seconds, as the dip tank is moved from dashed line C to dashed line T, so that the lowering of the dip tank allows for melting of the first 255 and second 257 petrolatum coatings, such that the first 255 and second 257 coatings gradually curve inward, providing shape to a portion of the intermediate bulbous portion 44", as shown in FIG. 20. Once at dashed line T, lowering (pull-back) pauses (in a dwell) for approximately two minutes as the first 255 and second 257 petrolatum coatings are melted off of (stripped from) the intermediate tip region 32", such that only the silicone elastomer coat (second polymeric coat 252) remains (FIG. 21).

(L) The pallet 112 is then automatically advanced to station 217 and stopped over a dip tank (similar to the dip tank 130 at station 201, as shown in FIG. 14), containing a volatile organic solvent such as toluene, trichloroethane or the like. The tank is then raised to immerse the coated mandrel 100 to the depth indicated by dashed line T, thereby removing essentially all traces of the petrolatum from this portion of the second polymeric coating 252. This step is preferably performed with a single, approximately four minute "dip" to enhance the silicone/silicone bond between the first 251 and second 252 polymeric coatings at the intermediate tip region 32", and to free the intermediate tip region 32" of petrolatum.

(M) The pallet 112 is then transported to station 218 where the intermediate structures 250 are dried for approximately ten minutes. The drying is by air, at approximately 15.5° C. (60° F.) being blown through the processing station 218.

(N) The pallet 112 is then automatically advanced to station 219 having a dip tank (similar to the dip tank 130 at station 201, as shown in FIG. 14), containing a hexamethyl disiloxane silicone rubber dispersion which is effective to minimize any disruption of the integrity of the petrolatum (or petroleum jelly) coatings remaining on the intermediate structure 250. Although the present apparatus 20 can be constructed of any suitable, medically acceptable, polymeric material, medical grade silicone rubber is preferred. The silicone rubber of the sleeve overcoat preferably is soft, with a hardness of about 20 to 40 durometer, more preferably about 30 durometer. It will be appreciated that such a silicone rubber polymeric coating layer must be fully cured prior to sale or use of the apparatus 20. The overcoat layer 24 can have a thickness of about 0.05 mm to 0.77 mm (0.002 in to 0.030 in), preferably about 0.13 mm (0.005 in) plus or minus 0.05 mm (0.002 in). The preferred uncured silicone rubber dispersion is a very soft uncured silicone rubber dissolved in weak solvent that will not disrupt the petrolatum or petroleum jelly. An effective uncured silicone rubber dispersion for making the present invention is a 25–75 mixture of uncured silicone rubber in hexamethyl disiloxane. This mixture is made of GE 6030 or Dow-Corning Q7-4850 in hexamethyl disiloxane. The dip tank is then raised to immerse essentially the entire length of the intermediate structure 250 in the silicone mixture to dashed line M, and then lowered, to complete the "dip". The "dip" lasts for approximately 45 seconds, resulting in the intermediate structure 250, shown in FIG. 22, having a third polymeric coating 261. This dip is followed by an air-dry, lasting approximately two to two and one half minutes, as air at approximately 21° C. (70° F.) is blown through the processing station 219. The "dip" and subsequent air-drying steps are repeated, preferably two times, such that this third polymeric coating 261 (that ultimately serves as the overcoat layer 24), as a result of these "dips" and "dries" becomes rounder at the intermediate bulbous portion 44".

(O) The pallet 112 is then moved to an empty station 220, where the coated mandrels 100 dry in the ambient environment.

(P) The pallet 112 is then transported to stations 221–225 where the intermediate structures 250 are dried for approximately 50 minutes. The drying is by air, at approximately 21° C. (70° F.) being blown through the processing stations 221–225.

(Q) The pallet 112 is then lowered into a tank at a constant height, the tank occupying stations 226–231, and filled with hot USP petrolatum at approximately 116° C. (240° F.). The intermediate structures 250 (FIG. 22) on the mandrels 100 are immersed up to dashed line M and advanced at that level for approximately one hour, before removal from this stationary tank. This processing step serves to cure the third polymeric coating 261, placed onto the intermediate structure 250 at step (N) above, without disrupting the shape of the structure as would occur with a hot air oven (as is done conventionally).

(R) The now formed intermediate structures 250 (body members 21) are then preferably taken off of the production line (stations 201–213) and in a separate production step, are soaked for preferably about 24 to 36 hours, in a hot bath of mineral oil at about 116° C. (240° F.). The mineral oil will generally replace the petrolatum coatings 255, 257 (FIGS. 19 and 20), encased within the third polymeric coating 261 (FIG. 22), by osmosis, after this period of time, and the mineral oil will remain a liquid at room temperature. The mineral oil has a significantly lower viscosity than petrolatum at room temperature. A different fluid such as water, sterile saline, glycerin, polyethylene glycol, gas (e.g., air) and the like, or appropriate mixtures thereof may also be substituted for the mineral oil/ petrolatum fluid in alternate embodiments by removing most of the latter liquid, and then inserting the former by appropriate means.

(S) The now completed body members 21 are then loaded with a stylet 28 (FIG. 1), sterilized by conventional sterilization techniques, e.g. steam, ethylene oxide vapor, irradiation, or the like, and packaged by packaging techniques known in the medical device art. If desired, this package can be sold as a kit commercially.

The above described method for producing the body members 21 (polymeric structures) of the present invention allows for the manufacture of these devices at the rate of about 2,400 pieces per hour. Because minimal, if any, hand work is involved, the body members 21 will be produced with consistency, high quality and economically.

While the invention has been described in connection with an embodiment, it will be understood that the invention is not limited to that embodiment. The invention is intended to cover all alternatives, modifications and equivalents as may be included within the spirit and scope thereof, as determined by the claims.

What is claimed is:

1. A device for use within a patient's urinary tract for blocking the flow of urine therein, comprising:

a deformable body member adapted for at least partial insertion into at least the urethra, said body member having a shape retaining memory and including a deformable fluid filled cavity, said fluid filled cavity extending along said body member, and having a proximal end and a distal end;

at least a portion of said body member having an at rest diameter greater than that of an undilated urethra of the patient's urinary tract, said body member including a distally positioned bulbous portion and a proximally positioned sleeve portion, the diameter of the bulbous portion at its widest point being greater than the diameter of the sleeve portion.

2. The device of claim 1, wherein said fluid filled cavity is constructed and arranged to deform upon insertion of said body member into the urethra, and upon said continued insertion of said body member through said urethra into at least the bladder neck, at least a portion of said fluid filled cavity at said distal end expands toward a diameter at least as great as said rest diameter, as the pressure from the walls of said urethra compress on at least a portion of said fluid filled cavity at said proximal end, causing fluid flow toward the distal end of the fluid filled cavity.

3. The device of claim 2, wherein said fluid filled cavity is further constructed and arranged to deform upon insertion into the urethra to permit fluid flow from said distal end of said fluid filled cavity toward the proximal end of said fluid filled cavity.

4. The device of claim 3, additionally including means for initiating fluid flow in the fluid filled cavity toward the proximal end of the fluid filled cavity, when the device is removed from the urinary tract.

5. The device of claim 3, wherein said initiating means includes a handle at an end of the body member, proximate the proximal end of said cavity, said handle allowing the user to deform the cavity for fluid flow between the proximal and distal ends of the fluid filled cavity and to remove the body member from the urinary tract.

6. The device of claim 5, wherein said fluid in said fluid filled cavity is a liquid.

7. The device of claim 5, wherein said fluid in said fluid filled cavity is a gas.

8. A device for use within a patient's urinary tract for blocking the flow of urine therein, comprising:

a body member having an elastic segment;

said elastic segment having a shape retaining memory, extending substantially along the entire length of the body member, and including a bulbous portion distally positioned on the body member and a sleeve portion proximally positioned on the body member; and said elastic segment being deformable between a first position at rest and a second deployment position in the urinary tract;

said elastic segment in said first position having a first diameter equal to or greater than the diameter of the undilated urethra of the patient's urinary tract, and, in said first position, the diameter of the bulbous portion at its widest point being greater than the diameter of the sleeve portion; and said elastic segment during transition from said first position to said second position being subject to urethral wall pressure, where the diameter of the elastic segment decreases such that it is less than said first diameter, and once in said second position, at least a portion of said elastic segment extends into the bladder neck of said patient's urinary tract for anchorage of said device, said at least a portion of said elastic segment expanding toward said first diameter.

9. The device of claim 8, wherein said body member includes a proximal end and a distal end, said body member additionally comprising a handle member attached to the proximal end, the deformation of said device upon withdrawal from the urinary tract being initiated by manipulation of the handle member.

10. The device of claim 9, wherein the body member additionally comprises a tube and the elastic segment comprises an overcoat layer encircling the tube; and a fluid filled cavity intermediate the overcoat layer and the tube, said overcoat layer sealing the fluid in the fluid filled cavity.

11. The device of claim 10, wherein the fluid in the fluid filled cavity is liquid.

12. The device of claim 10, wherein the fluid in the fluid filled cavity is a gas.

13. A device for deployment within a human patient's urinary tract to block the flow of urine therethrough, comprising:

a shaft, said shaft having an inner bore and an outer surface and a proximal end and a distal end;

an overcoat layer having a shape retaining memory encircling at least a portion of said shaft and extending substantially along said shaft, said overcoat layer including a bulbous portion distally positioned on the shaft and a sleeve portion proximally positioned on the shaft, the diameter of the bulbous portion at its widest point being greater than the diameter of the sleeve portion, at least a portion of said overcoat layer being of a diameter at least as great as the diameter of an undilated urethra of the patient's urinary tract;

said overcoat layer and shaft defining a continuous cavity intermediate said outer surface of said shaft and said overcoat layer, said cavity having a volume filled at least in part with a fluid, said overcoat layer being elastically deformable to allow for movement of said fluid within said cavity during deployment, the cavity volume remaining substantially constant upon said deployment.

14. The device of claim 13, wherein said shaft additionally comprises a stopper member at the proximal end of the shaft, the stopper member having a diameter greater than the diameter of the shaft.

15. The device of claim 14, wherein the stopper member and the shaft are integral.

16. The device of claim 14, additionally comprising a stylet, removably inserted into the inner bore.

17. The device of claim 16, wherein the stylet includes an end member of a length greater than the perimeter of the inner bore.

18. The device of claim 14, wherein said shaft is closed at said distal end.

19. The device of claim 14, wherein said shaft includes at least one opening at said distal end.

20. The device of claim 13, wherein the proximal end of the shaft and the distal end of the shaft extend beyond the overcoat layer.

21. The device of claim 20, wherein the overcoat layer proximate to the distal end of the shaft includes a first portion, said first portion corresponding to a first portion of said continuous cavity having a first volume, and a second portion, said second portion corresponding to a second portion of said continuous cavity having a second volume, said first volume and said second volume being variable during deployment.

22. The device of claim 21, wherein said first portion has a bulbous shape and said second portion has a generally cylindrical shape, said first volume being greater than said second volume.

23. A device for use within a patient's urinary tract comprising:

a shaft; and a deformable member having a shape retaining memory encircling said shaft along at least a portion of said shaft, said deformable member having a continuous inner body, said deformable member including a bulbous portion distally positioned on the shaft and a sleeve portion proximally positioned on the shaft, a diameter of the bulbous portion at its widest point being greater than a diameter of the sleeve portion;

at least a portion of said deformable member having a diameter at least as great as the diameter of an undilated urethra of the patient's urinary tract.

24. The device of claim 23, wherein said shaft includes a proximal end and a distal end and said deformable member includes a first portion proximate said distal end and a second portion proximate said proximal end, said first and second portions of said overcoat layer and said shaft defining said inner body of said deformable member.

25. The device of claim 24, wherein said fluid filled cavity comprises substantially all of the volume of said deformable member.

26. The device of claim 23, wherein said shaft includes a proximal end and a distal end, said shaft being closed at said distal end.

27. The device of claim 23, wherein said shaft includes a proximal end and a distal end, said shaft including at least one opening at said distal end.

28. A device for use within a patient's urinary tract for blocking the flow of urine therein, comprising:

a deformable body member adapted for at least partial insertion into at least the urethra, said body member including at least a portion having an at rest diameter greater than that of an undilated urethra of the patient's urinary tract and being deformable, such that voidance dislodges the device from the patient's urinary tract.

29. A device for use within a patient's urinary tract comprising:

a deformable body member including an overcoat layer;

said overcoat layer having a shape retaining memory and encasing a continuous fluid filled cavity, said overcoat layer including a bulbous portion distally positioned on the body member and a sleeve portion proximally positioned on the body member, the diameter of the bulbous portion at its widest point being greater than the diameter of the sleeve portion, at least a portion of the overcoat layer having a diameter at least as great as the diameter of an undilated urethra of the patient's urinary tract, said deformable member adaptable to the shape of the urinary tract upon deployment therein to block the flow of urine therefrom, said overcoat layer positioned on said deformable body member, such that once said deformable body member is deployed in at least the urethra, to block the flow of urine therethrough, said overcoat layer is adapted to be in the patient's urinary tract in at least the urethra.

30. A device for use within a patient's urinary tract for blocking the flow of urine therein, comprising:

a deformable body member having a shape retaining memory and being adapted for at least partial insertion into at least the urethra, said body member including a resiliently deformable fluid filled cavity, said fluid filled cavity extending along said body member and having a proximal end and a distal end, at least a portion of said body member having an at rest diameter greater than that of an undilated urethra of the patient's urinary tract, said body member including a distally positioned bulbous portion and a proximally positioned sleeve portion, a diameter of the bulbous portion at its widest point being greater than a diameter of the sleeve portion.

31. A device for use within a patient's urinary tract for blocking the flow of urine therein, comprising:

a deformable body member having a shape retaining memory and being adapted for at least partial insertion into at least the urethra, said body member including a deformable fluid filled cavity, said fluid filled cavity being uninterrupted by a valve or clamp, extending along said body member, and having a proximal end and a distal end, at least a portion of said body member having an at rest diameter greater than that of an undilated urethra of the patient's urinary tract, said body member including a distally positioned bulbous portion and a proximally positioned sleeve portion, a diameter of the bulbous portion at its widest point being greater than a diameter of the sleeve portion.

32. The device of claim 31, wherein the fluid filled cavity is uninterrupted by an internal valve.

33. The device of claim 31, wherein the fluid filled cavity is uninterrupted by an external valve.

34. A device for use within a patient's urinary tract for blocking the flow of urine therein, comprising:

a deformable body member having a shape retaining memory and being adapted for at least partial insertion into at least the urethra, said body member including a deformable fluid filled cavity, said fluid filled cavity extending along said body member and having a proximal end and a distal end, at least a portion of said body member having an at rest diameter greater than that of an undilated urethra of the patient's urinary tract, said body member including a distally positioned bulbous portion and a proximally positioned sleeve portion, a diameter of the bulbous portion at its widest point being greater than a diameter of the sleeve portion, the location of the fluid within the cavity being determined by external pressure on the device.

35. The device of claim 34, wherein a source of the external pressure is the patient's urethra, the patient's bladder, manipulation by the patient, or a combination thereof.

* * * * *